US012747879B2

(12) United States Patent
Lee et al.

(10) Patent No.: US 12,747,879 B2
(45) Date of Patent: Sep. 29, 2026

(54) HUMIDIFIER

(71) Applicant: LG ELECTRONICS INC., Seoul (KR)

(72) Inventors: Kunyoung Lee, Seoul (KR); Kyunglok Cho, Seoul (KR); Sunyoung Moon, Seoul (KR); Wonjun Jeong, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 286 days.

(21) Appl. No.: 18/647,054

(22) Filed: Apr. 26, 2024

(65) Prior Publication Data

US 2024/0361023 A1 Oct. 31, 2024

(30) Foreign Application Priority Data

Apr. 27, 2023 (KR) ........................ 10-2023-0055139

(51) Int. Cl.
*F24F 6/12* (2006.01)
*A61L 9/20* (2006.01)
(Continued)

(52) U.S. Cl.
CPC .................. *F24F 6/12* (2013.01); *A61L 9/20* (2013.01); *B01D 46/0004* (2013.01);
(Continued)

(58) Field of Classification Search
None
See application file for complete search history.

(56) References Cited

U.S. PATENT DOCUMENTS 8,940,085 B2 * 1/2015 Markham ................. F24F 8/22 261/78.2
2012/0319311 A1 * 12/2012 Nutter ....................... A61L 9/20 250/437
(Continued)

FOREIGN PATENT DOCUMENTS

EP 4455570 A1 * 10/2024 ............. F24F 13/28
KR 10-0158806 1/1999
(Continued)

OTHER PUBLICATIONS

EP-455570 (Year: 2024).*
(Continued)

*Primary Examiner* — Brit E. Anbacht
(74) *Attorney, Agent, or Firm* — KED & ASSOCIATES, LLP

(57) ABSTRACT

A humidifier according to an embodiment of the present disclosure includes: a case; a base disposed below the case; a base cover which is disposed above the base, and to which the case is removably coupled; a humidifying assembly disposed in the case and configured to generate mist, a filter disposed below the humidifying assembly; and a sterilization module disposed on the base cover and configured to emit ultraviolet light, wherein in response to the case being coupled to the base cover and the filter being seated, the sterilization module is configured to emit ultraviolet light to an inner hollow of the filter, thereby preventing a safety accident, and controlling hygiene in the humidifier.

18 Claims, 17 Drawing Sheets

(51) Int. Cl.

*B01D 46/00* (2022.01)
*F24F 8/10* (2021.01)
*F24F 13/28* (2006.01)

(52) U.S. Cl.

CPC ..... *B01D 46/0028* (2013.01); *B01D 46/0041* (2013.01); *F24F 8/10* (2021.01); *F24F 13/28* (2013.01); *A61L 2209/12* (2013.01); *A61L 2209/14* (2013.01); *B01D 2279/40* (2013.01)

(56) References Cited

U.S. PATENT DOCUMENTS

| | | | | |
|---|---|---|---|---|
| 2024/0361023 | A1* | 10/2024 | Lee | F24F 8/22 |
| 2025/0067450 | A1* | 2/2025 | Van Deventer | F24F 11/77 |

FOREIGN PATENT DOCUMENTS

| | | |
|---|---|---|
| KR | 10-1632296 | 6/2016 |
| KR | 10-1680308 | 11/2016 |
| KR | 10-2018-0088558 | 8/2018 |
| KR | 10-2264454 | 6/2021 |
| KR | 10-2021-0138353 | 11/2021 |
| KR | 10-2022-0022038 | 2/2022 |
| KR | 10-2473432 | 12/2022 |
| WO | WO 2022/085871 | 4/2022 |

OTHER PUBLICATIONS

Extended European Search Report dated Aug. 28, 2024 issued in Application No. 24172342.8.

Korean Office Action dated Jul. 2, 2025, issued in Application No. 10-2023-0055139.

* cited by examiner

HUMIDIFIER

CROSS-REFERENCE TO RELATED APPLICATION(S)

This application claims priority under 35 U.S.C. § 119 to Korean Application No. 10-2023-0055139, filed in Korea on Apr. 27, 2023, whose entire disclosure(s) is/are hereby incorporated by reference.

BACKGROUND

1. Field

The present disclosure relates to a humidifier to supply humidified air.

2. Background

A humidifier is a device that may supply moisture-containing humidified air to an interior space. The humidifier may include a water tank, and may be classified into various types, such as ultrasonic humidifiers, heated humidifiers, evaporative humidifiers, or complex humidifiers, depending on humidification methods used by the humidifier to convert the water in the tank into the humidified air. For example, a humidifier may vaporize water in the tank to form humidified air with high moisture content, and the humidifier may generate humidified air by evaporating water using natural vaporization, heating vaporization, and/or ultrasonic vibration.

Each evaporation method has its own merits and disadvantages. As an example, an evaporative humidification method may use a humidifying medium that draws water over a larger surface area for faster evaporation, but a user may need to frequently clean or replace the humidifying medium to maintain performance and cleanliness. In another example, heating vaporization may cause relatively hot humidified air to be directly discharged into the indoor space, but potentially allowing a safety accident to occur.

The ultrasonic humidifier may include a vibrator to generate ultrasonic waves, and humidified air may be formed by water that is atomized by the ultrasonic waves. The ultrasonic humidifier may output a relatively large amount of mist, but air that is humidified by atomizing supplied water by ultrasonic vibration may not effectively flow into an indoor space. Additionally, if unsterilized water is used for humidification, air carrying the unsterilized water may flow into the indoor space, and the ultrasonic vibrator may be vulnerable damage from high-temperature heat.

Korean Patent No. KR 10-0158806 provides an example of a humidifier for humidifying water, supplied from a water tank, by heating and ultrasonic vibrations. However, this and other known humidifiers of this type may cause sanitary conditions due to contamination of water remaining in the humidifier, such that air sprayed from the humidifier may spread the contaminated water.

In addition, the humidifier may provide clean air by using a filter provided therein for filtering intake air. In a structure in which external air is introduced and flows therein, bacteria or microbes may be accumulated in the filter or a fan disposed in an air purifier, thereby causing a potential problem in that when air is discharged to an indoor space, the bacteria or microbes may be contained in the air. Korean Laid-Open Patent Publication No. KR 10-2021-0138353 provides an example of a lamp for sterilizing a filter, but does not provide a specific arrangement or structure thereof, and has a disadvantage that bacteria or microbes may accumulate over time, thereby resulting in deterioration of air purification performance of the filter. Accordingly, active research is being conducted on comprehensive methods for keeping the inside of the humidifier clean and sanitary.

The above references are incorporated by reference herein where appropriate for appropriate teachings of additional or alternative details, features and/or technical background.

BRIEF DESCRIPTION OF THE DRAWINGS

Embodiments will be described in detail with reference to the following drawings in which like reference numerals refer to like elements, and wherein.

DETAILED DESCRIPTION

Figure 1:
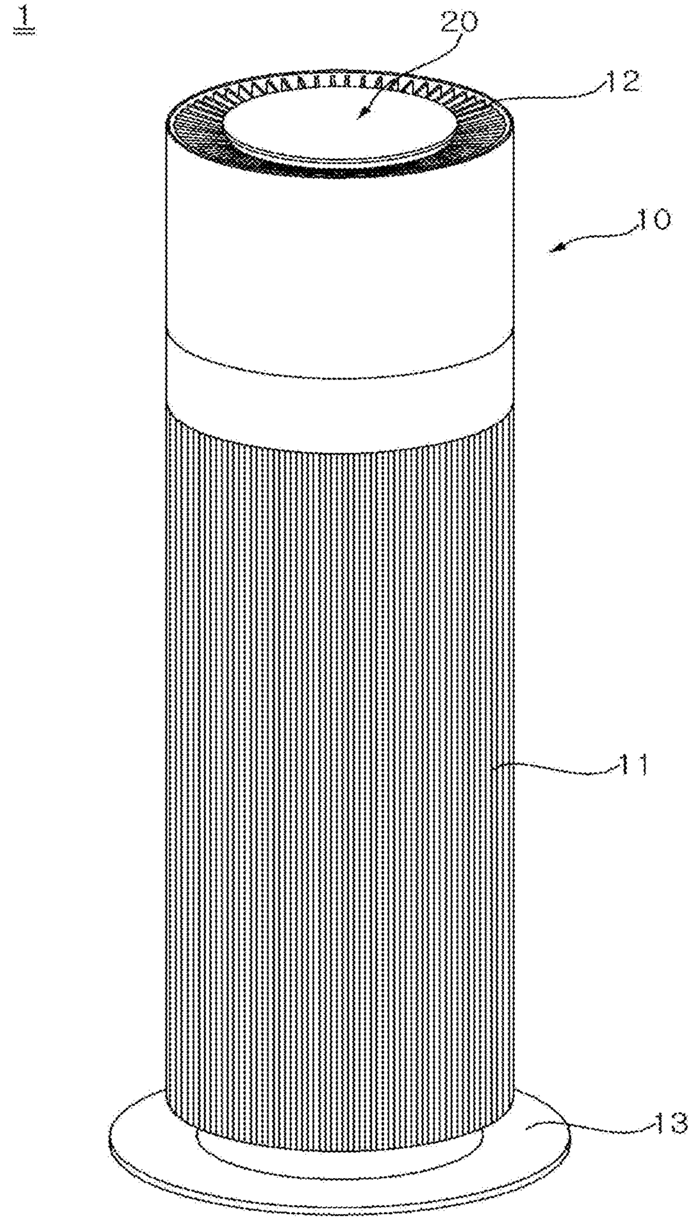
FIG. 1 is a perspective view of a humidifier according to an embodiment.

Hereinafter, the present disclosure will be described in detail with reference to the accompanying drawings, in which the same reference numerals are used throughout the drawings to designate the same or similar components, and a redundant description thereof will be omitted. The terms "module" and "unit" for elements used in the following description are given simply in view of the ease of the description, and do not have a distinguishing meaning or role.

It will be noted that a detailed description of known arts will be omitted if it is determined that the detailed description of the known arts can obscure the embodiments of the invention. Further, the accompanying drawings are used to help easily understand various technical features and it should be understood that the embodiments presented herein are not limited by the accompanying drawings. As such, the present disclosure should be construed to extend to any alterations, equivalents and substitutes in addition to those which are particularly set out in the accompanying drawings.

It will be understood that, although the terms first, second, etc., may be used herein to describe various elements, these elements should not be limited by these terms. These terms are only used to distinguish one element from another. It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. As used herein, the singular forms are intended to include the plural forms as well, unless the context clearly indicates otherwise.

Referring to FIG. 1, aspects of a humidifier 1 will be described below. FIG. 1 is a perspective view of the humidifier 1 according to certain implementations of an embodiment.

The humidifier 1 may include a case 10. The case 10 may have a space formed therein. The case 10 may have a cylindrical or other shape.

The humidifier 1 may include a suction port or inlet 11. The suction port 11 may be formed along the circumference of the case 10, but may be provided in other locations. Air from outside the humidifier 1 may be introduced into the case 10 through the suction port 11.

The humidifier 1 may include a discharge port or outlet 12. The discharge port 12 may be formed at a top portion of the case 10 or at other locations. The air drawn into the case 10, such as through suction port 11, may be discharged to the outside of the case 10 through the discharge port 12.

The humidifier 1 may include a base 13. The base 13 may be disposed at the bottom of the case 10. The base 13 may have a greater outer diameter than an outer diameter of the case 10.

The humidifier 1 may include a water tank 20. The water tank 20 may be disposed in the case 10. The water tank 20 may have a space in which water is contained. The discharge port 12 may be formed radially outside of the water tank 20. The discharge port 12 may be formed to surround the water tank 20.

Figure 2:
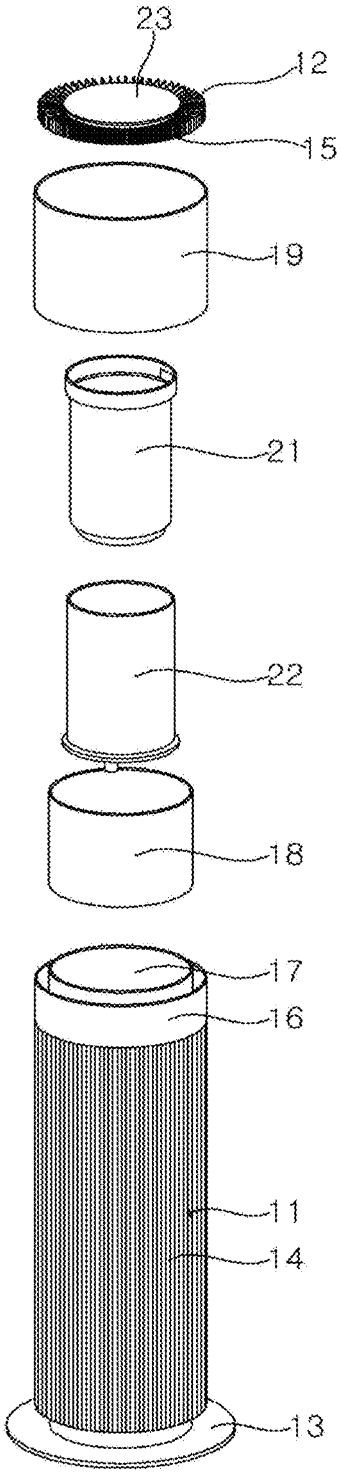
FIG. 2 is an exploded view of a humidifier according to an embodiment.

Referring to FIG. 2, aspects of the humidifier 1 will be described below. FIG. 2 is an exploded view of the humidifier 1 in certain implementations.

The humidifier 1 may have a suction grill 14. The suction grill 14 may be disposed along the circumference of the case 10. The suction grill 14 may form the suction port 11. The suction grill 14 may have a substantially cylindrical shape or other shape to correspond to the case 10.

The humidifier 1 may include a discharge grill 15. The discharge grill 15 may be disposed at a top portion of the case 10. The discharge grill 15 may form at least a portion of the discharge port 12. The discharge grill 15 may have an annular shape.

The humidifier 1 may include a first outer case 16. The first outer case 16 may have a substantially cylindrical or other shape. The suction grill 14 may be removed from the first outer case 16. The first outer case 16 may form at least a portion of the exterior of the case 10.

The humidifier 1 may include a first inner case 17. The first inner case 17 may have a substantially cylindrical or other shape. The first inner case 17 may be disposed radially inside of the first outer case 16. The first outer case 16 and the first inner case 17 may be radially spaced apart from each other, such as to define an air passage therebetween.

The humidifier 1 may include a second outer case 19. The second outer case 19 may have a substantially cylindrical or other shape. The second outer case 19 may be disposed on top of the first outer case 16. The second outer case 19 may form a portion of the exterior of the case 10.

The humidifier 1 may include a second inner case 18. The second inner case 18 may have a substantially cylindrical or other shape. The second inner case 18 may be disposed on top of the first inner case 17. The second inner case 18 may be disposed radially inside of the second outer case 19. The second outer case 19 and the second inner case 18 may be radially spaced apart from each other, such as to define an air passage therebetween.

The first outer case 16 and the second outer case 19 may be removably coupled to each other. However, the first outer case 16 and the second outer case 19 may be integrally formed with each other. The first outer case 16 and the second outer case 19 may be referred to as an "outer case."

The first inner case 17 and the second inner case 18 may be removably coupled to each other. However, the first inner case 17 and the second inner case 18 may be integrally formed with each other. The first inner case 17 and the second inner case 18 may be referred to as an "inner case."

The humidifier 1 may include a bucket 21. The bucket 21 may have a substantially cylindrical or other shape with an open top. The bucket 21 may have a space formed therein for storing water received through the open top.

The humidifier 1 may include a bucket housing 22. The bucket housing 22 may surround the bucket 21. The bucket housing 22 may have a substantially cylindrical or other shape with an open top. The bucket 21 may be disposed in the bucket housing 22.

The humidifier 1 may include a bucket cover 23. The bucket cover 23 may be disposed on top of the bucket 21. The bucket cover 23 may be removably coupled to the discharge grill 15.

The water tank 20 may include the bucket 21, the bucket housing 22, and the bucket cover 23. The water tank 20 may be disposed inside the inner case 18. The water tank 20 and the inner case 18 may be radially spaced apart from each other.

Figure 3:
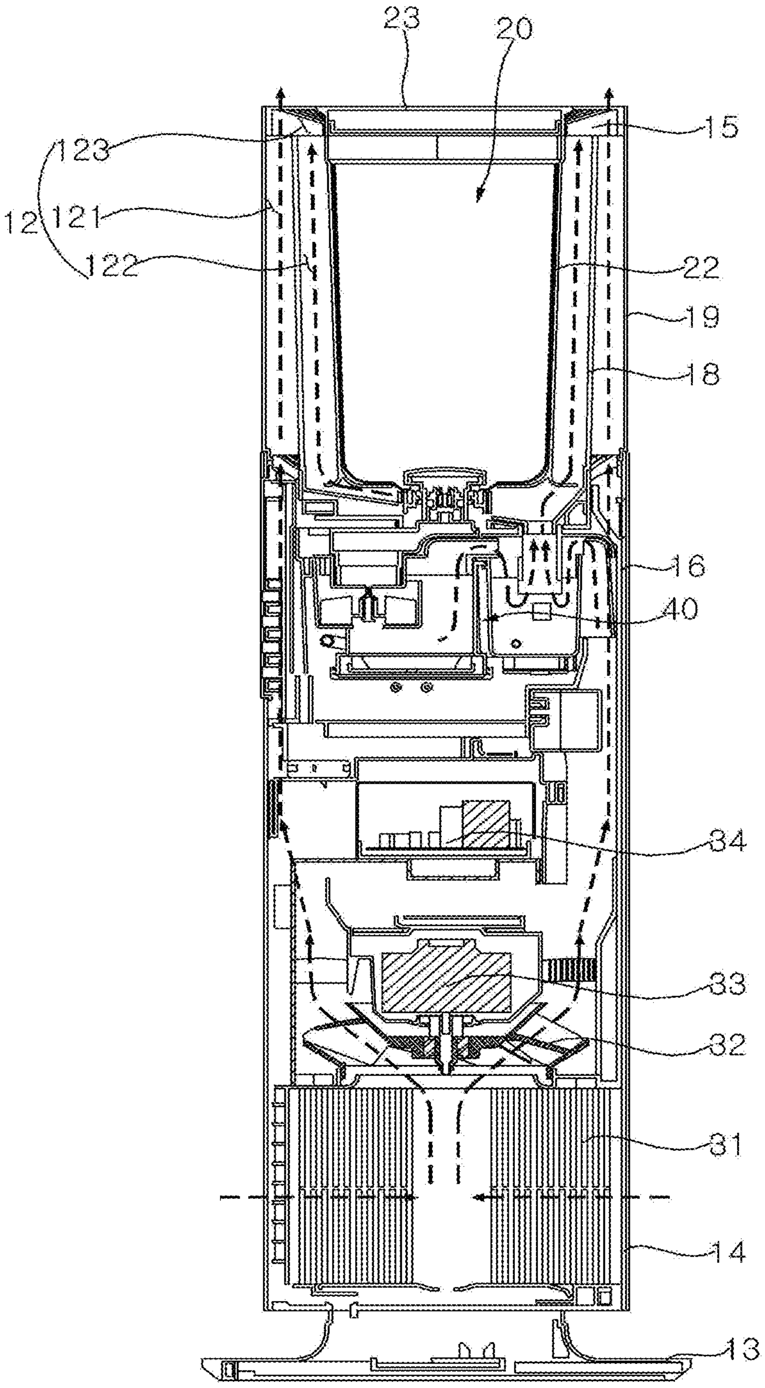
FIG. 3 is a cross-sectional view of a humidifier according to an embodiment.

Referring to FIG. 3, aspects of the humidifier 1 will be described below. FIG. 3 is a vertical cross-sectional view of the humidifier 1 in certain implementations.

The humidifier 1 may include a filter 31 that filter air entering the humidifier 1, such as through such as through suction port 11. The filter 31 may be disposed adjacent to and/or radially within the suction grill 14. The filter 31 may have a substantially cylindrical or other shape to be provided downstream of suction grill 14.

The humidifier 1 may include a fan or blower 32. The fan 32 may be disposed above or otherwise downstream of the filter 31 to receive filtered air. The fan 32 may be disposed radially within in the suction grill 14, such as within or above filter 31.

The humidifier 1 may include a fan motor 33. The fan motor 33 may provide a force to rotate the fan 32. The fan motor 33 is coupled to the fan 32 to provide the driving force and, in one example, may be disposed above the fan 32.

The humidifier 1 may include a controller 34. The controller 34 may be disposed in the case 10. The controller 34 may be disposed between the fan motor 33 and a humidifying assembly 40. The controller 34 may control driving of the fan motor 33 and the humidifying assembly 40. The controller 34 may include one or more processors. The controller 34 may include one or more printed circuit boards (PCBs). In another example, the controller 34 may be provided in a separate device, such as a computing or user device coupled to the humidifier through a wired or wireless connection.

The humidifier 1 may include the humidifying assembly 40. The humidifying assembly 40 may be disposed in the case 10. The humidifying assembly 40 may be disposed between the water tank 20 and the fan 32. The humidifying assembly 40 may atomize water supplied from the water tank 20 and supply the atomized water toward the discharge port 12. A portion of air blown by the fan 32 may be introduced into the humidifying assembly 40 and may carry the atomized water as a mist outputted through the discharge port 12.

The discharge grill 15 may be disposed radially between the water tank 20 and the outer case 19. The inner case 18 may be disposed between the water tank 20 and the outer case 19. The discharge grill 15 may be disposed at the top of the inner case 18.

Figure 18:
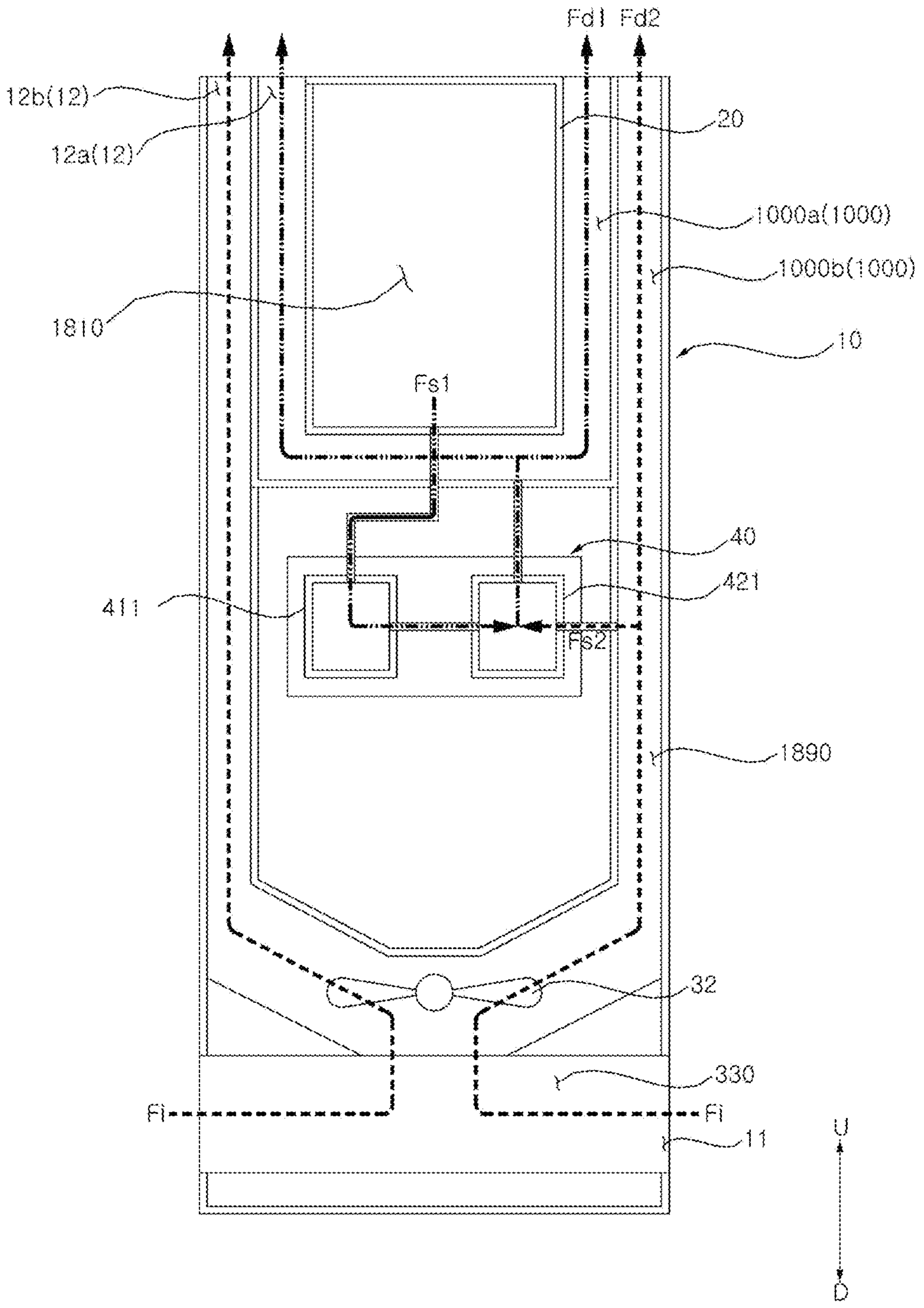
FIG. 18 is a schematic view of a humidifier according to an embodiment.

The discharge port 12 may include a first discharge port (or air blowing passage) 121 or 12*a* (see FIG. 18). The first discharge port 121 may be formed between the outer case 19 and the inner case 18. A portion of the air blown by the fan 32 may flow upward through the first discharge port 121 without being humidified. The first discharge port 121 may extend annularly. The first discharge port 121 may be referred to as a "air-blowing passage." In addition, the first discharge port 121 may be coupled to a first discharge passage 1000*a* to receive air from fan 32.

The discharge port 12 may include a second discharge port (or humidification passage) 122 or 12*b* (See FIG. 18). The second discharge port 122 may be formed between the inner case 18 and the water tank 20. A portion of the air blown by the fan 32 may flow through the humidifying assembly 40 to be humidified, and the humidified air, having passed through the humidifying assembly 40, may flow upward through the second discharge port 122. The second discharge port 122 may extend annularly. The second discharge port 122 may be referred to as a "humidification passage." In addition, the second discharge port 122 may be coupled to a second discharge passage 1000*b*.

The discharge port 12 may include a combined outlet 123. The combined outlet 123 may be formed at the top of the first discharge port 121 and the second discharge port 122. The combined outlet 123 may be formed in the discharge grill 15. The combined outlet 123 may extend annularly. The combined outlet 123 may be formed between the outer case 19 and the bucket cover 23. Air flowing to the first discharge port 121 and air flowing to the second discharge port 122 may be mixed at the combined outlet 123.

The discharge port 12 may conceptually include the first discharge port 121, the second discharge port 122, and the combined outlet 123. Additionally, the discharge port 12 may refer to a space which is open toward the outside of the case 10, and which is separate from the above ports 121, 122, and 123. The discharge port 12 may be open toward the top of the case 10. The discharge port 12 may be formed in or around the discharge grill 15. The discharge port 12 may be formed to surround the water tank 20. The air blown by the fan 32 may flow through the discharge port 12.

The air-blowing passage 121 may be connected to the discharge port 12. A humidification passage 122 may be connected to the discharge port 12. The air in the air-blowing passage 121 and the air in the humidification passage 122 may be mixed at the discharge port 12.

The air introduced into the case 10 through the suction grill 14 may pass through the filter 31 to be blown upward by the fan 32. A portion of the air blown upward by the fan 32 may be introduced into the humidifying assembly 40, and a remaining portion of the air may flow upward through the first discharge port 121. The air introduced into the humidifying assembly 40 may flow upward through the second discharge port 122 while containing atomized water droplets. The air flowing through the first discharge port 121 and the humidified air flowing through the second discharge port 122 may join at the combined outlet 123 to be discharged upward from the humidifier 1.

Figure 4:
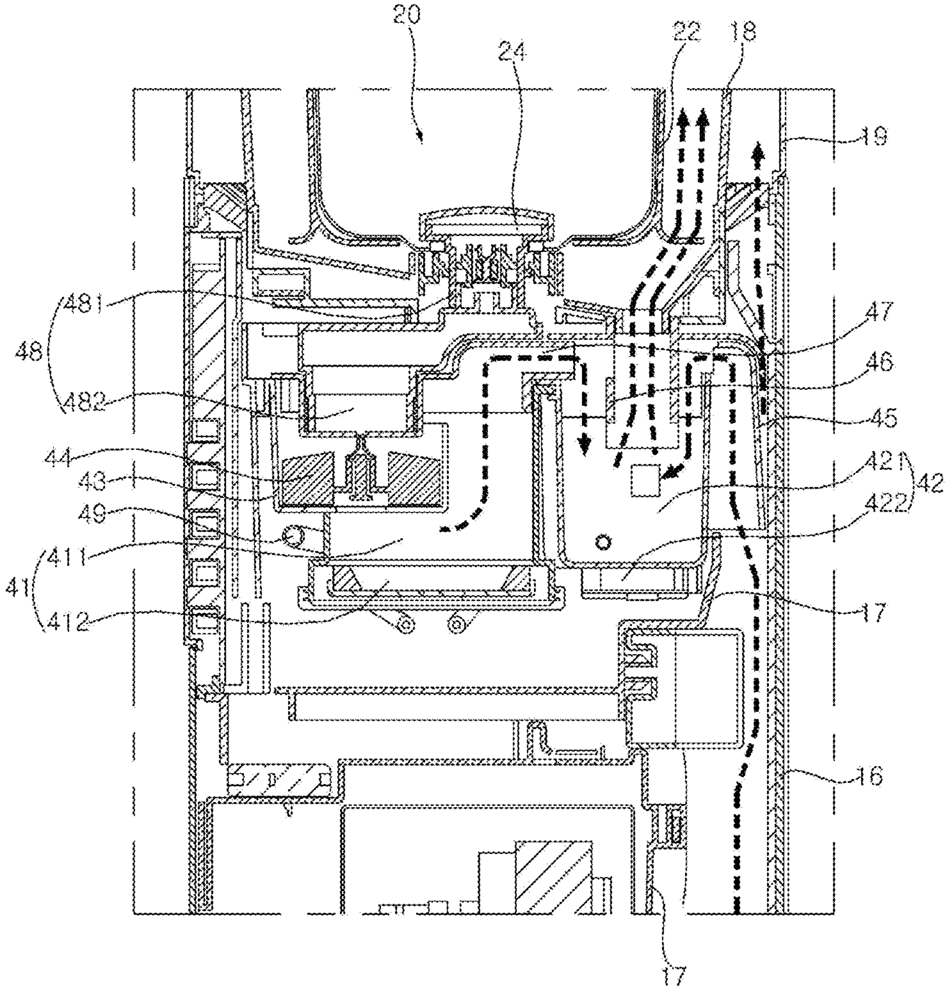
FIG. 4 is an enlarged cross-sectional view of a humidifier according to an embodiment.

Referring to FIG. 4, aspects of the humidifier 1 will be described below. FIG. 4 is a vertical cross-sectional view of a portion of the humidifier 1 in certain implementations.

The humidifier 1 may include the humidifying assembly 40 to generate humidified air. The humidifying assembly 40 may be disposed below the water tank 20. The humidified air generated in the humidifying assembly 40 may be discharged upwards.

The humidifying assembly 40 may include a heating device 41. The heating device 41 may heat the introduced water and air.

The heating device 41 may include a heating chamber (or heating housing) 411. The heating chamber 411 may provide an internal space. A portion of the water contained in the water tank 20 may be introduced into the heating chamber 411.

The heating device 41 may include a heater (or heating element) 412. The heater 412 may be coupled to a lower side or other section of the heating chamber 411. The heater 412 may apply heat to the inside of the heating chamber 411. The heater 412 may heat the water and air introduced into the heating chamber 411.

The humidifying assembly 40 may include a humidifying device 42. In one example, the humidifying device 42 may atomize the introduced water into droplets. It should be appreciated that other known methods may be used to generate the water droplets, such as to evaporate the water. The humidifying device 42 may discharge the droplets upwards.

The humidifying device 42 may include a humidifying chamber (or humidifying housing) 421. The humidifying chamber 421 may provide an internal space. In certain implementations, water heated by the heating device 41 may be introduced into the humidifying chamber 421. Additionally or alternatively, the water contained in the water tank 20 may be introduced into the humidifying chamber 421 without being heated within heating device 41 or by a separate path that bypasses the heating device 41.

The humidifying device 42 may include an ultrasonic vibrator 422. The ultrasonic vibrator 422 may be coupled to a lower side or other region of the humidifying chamber 421. The ultrasonic vibrator 422 may generate vibrations using ultrasound. For example, ultrasonic vibrator 422 may be a sonic transducer, such as a piezoelectric transducer, to create a high frequency (e.g., 1-2 MHZ) mechanical oscillation in a film of water to form fine mist of droplets (e.g., water of about one micron in diameter). By driving the ultrasonic vibrator 422, the water in the humidifying chamber 421 may be atomized into droplets. Other known principles of the ultrasonic humidifier may also be applied to the humidifying device 42.

The humidifying assembly 40 may include a valve housing 43. The valve housing 43 may be coupled to the heating device 41. The valve housing 43 may be disposed in the heating chamber 411. Water from the water tank 20 may be introduced into the heating chamber 411 via the valve housing 43.

The humidifying assembly 40 may include a valve 44. The valve 44 may be a floating valve or other known device for controlling a flow of water from water tank 20. The valve 44 may be movably disposed in the valve housing 43. In one example, the valve 44 may move up and down in the valve housing 43 to selectively supply water into the heating chamber 41.

The humidifying assembly 40 may include an inlet (or inlet) 45. The inlet 45 may be connected to the humidifying device 42. The inlet 45 may be connected to the inside of the humidifying chamber 421. A portion of the air blown by the fan 32 (see FIG. 3) may be introduced into the humidifying chamber 421 through the inlet 45.

The humidifying assembly 40 may include an outlet 46. The outlet 46 may be connected to the humidifying device 42. The outlet 46 may project toward the inside of the humidifying chamber 421. The atomized water droplets generated in the humidifying device 42 may be carried in a flow of humidified air upward through the outlet 46.

The humidifying assembly 40 may include a connector (or conduit) 47. The connector 47 may connect the heating device 41 and the humidifying device 42. The connector 47 may connect the heating chamber 411 and humidifying chamber 421, such as to allow heated air and water vapor to move from the heating chamber 411 to the humidifying chamber 421. The connector 47 may face a portion of the outlet 46.

The humidifying assembly 40 may include a supply port 48. The supply port 48 may connect the water tank 20 and the heating device 41. Water in the water tank 20 may be introduced into the heating device 41 through the supply port 48. For example, water in the water tank 20 may flow through the supply port 48 and into the valve housing 43.

The supply port 48 may include a first (or upper) supply port 481. The first supply port 481 may be connected to the water tank 20 and may receive water from the water tank 20. The first supply port 481 may be connected to the lower side of the bucket housing 22.

The water tank 20 may include a discharge port 24. The discharge port 24 may be formed at a lower portion of the water tank 20. The discharge port 24 may be connected to the first supply port 481, and water may flow from the water tank 20 through discharge port 24 and to the first supply port 481.

The supply port 48 may include a second (or lower) supply port 482. The second supply port 482 may connect the first supply port 481 and the valve housing 43. Water introduced into the first supply port 481 may be introduced into the valve housing 43 through the second supply port 482.

The humidifying assembly 40 may include a connection pipe 49. The connection pipe 49 may connect the heating device 41 and the humidifying device 42. The connection pipe 49 may connect the heating chamber 411 and the humidifying chamber 421. A portion of water in the heating chamber 411 may be introduced into the humidifying chamber 421 through the connection pipe 49.

As previously described, a portion of air flowing between the outer case 16 and the inner case 17 may be introduced into the humidifying device 42 through the inlet 45. The air introduced into the humidifying device 42 may flow upward through the outlet 46 while containing the water droplets generated in the humidifying device 42. The air flowing upward through the outlet 46 may flow upward between the water tank 20 and the inner case 18 to be outputted at discharge port 12.

As previously described, water in the water tank 20 may be introduced into the valve housing 43 through the supply port 48. The water in the valve housing 43 may be introduced into the heating device 41 by movement of the valve 44. The water introduced into the heating device 41 may be heated by the heater 412. The water heated in the heating chamber 411 may be introduced into the humidifying chamber 421 through the connection pipe 49 to be heated and sterilized. The sterilized water introduced into the humidifying chamber 421 may be atomized into droplets by the ultrasonic vibrator 422. The atomized water droplets may flow upward through the outlet 46 along with the air introduced through the inlet 45.

Figure 5:
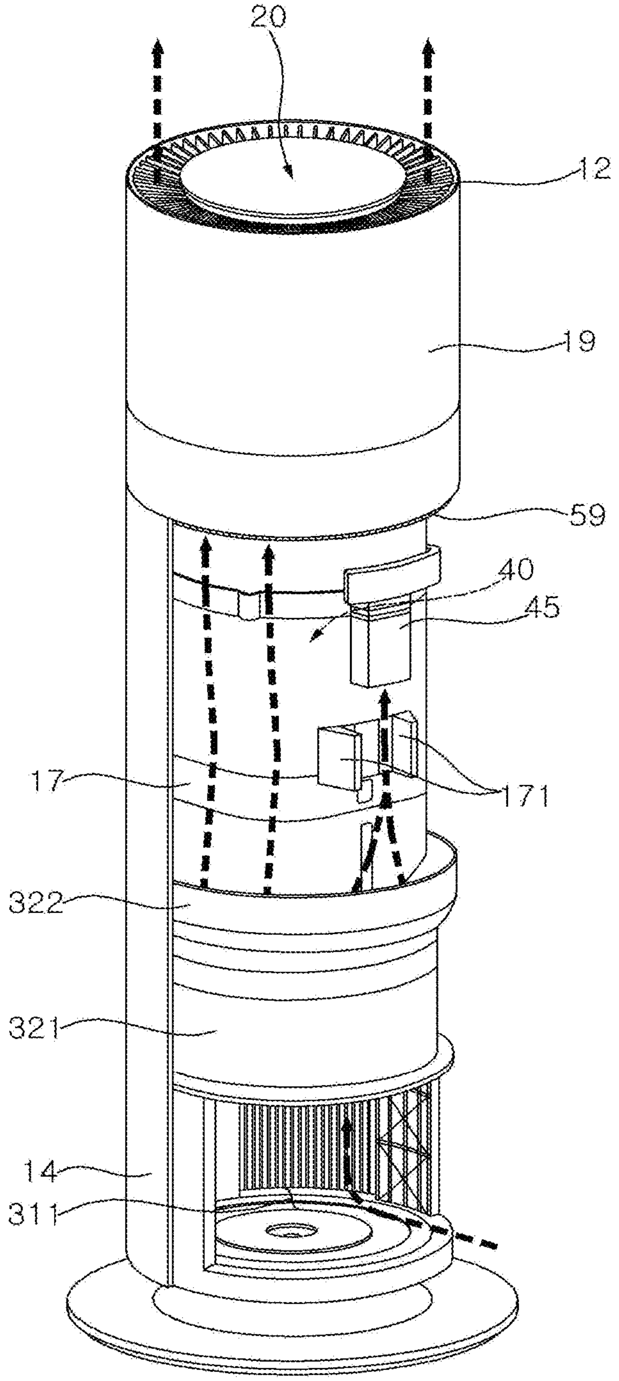
FIG. 5 is a diagram illustrating a portion of a humidifier according to an embodiment.

Referring to FIG. 5, aspects of the humidifier 1 will be described below. FIG. 5 is a diagram illustrating the humidifier 1 from which the first outer case 16 is separated, according to certain implementations.

The humidifier 1 may include a filter mounting space 311. The filter mounting space 311 may be formed in the suction grill 14. The filter 31 (see FIG. 3) may be disposed in the filter mounting space 311. The air introduced through the suction grille 14 may pass through the filter in the filter mounting space 311 and then flow upwards.

The humidifier 1 may include a fan housing 321. The fan 32 (see FIG. 3) may be disposed in the fan housing 321. The fan housing 321 may be disposed over or on top of the filter 31 (see FIG. 3). Air, after passing through the filter 31, may be suctioned into the fan housing 321 by the fan 32 through openings in a lower surface of the fan housing 321.

The humidifier 1 may include a housing top portion (or upper fan housing portion) 322. The housing top portion 322 may form a top portion of the fan housing 321. The housing top portion 322 may be radially outwardly spaced apart from the inner case 17 to guide air outputted from the fan housing 321. For example, the air blown by the fan 32 (see FIG. 3) may flow upward through a space formed between the inner case 17 and the housing top 322.

The humidifier 1 may include a guide 171. The guide 171 may protrude radially outward from the inner case 17. The guide 171 may be disposed between the inlet 45 and the fan housing 321. A plurality of the guides 171 may be arranged so as to be spaced apart in a circumferential direction of the inner case 17. A space between the plurality of guides 171 may by provided below and vertically face the inlet 45. The space between the plurality of guides 171 may vertically face the housing top portion 322.

The humidifier 1 may include an inner grill 59. The inner grill 59 may be disposed above the humidifying assembly 40. The inner grill 59 may be disposed radially outside of the inner case 17. The inner grill 59 may be coupled to the outer case 19.

A first portion of the air blown by the fan 32 (see FIG. 3) may be introduced into the inlet 45. The portion of the air blown by the fan 32 may be introduced into the inlet 45 through the space between the plurality of guides 171. The air introduced into the humidifying assembly 40 through the inlet 45 may be discharged through the discharge port 12 while transporting atomized water droplets.

In certain examples, a supporter may be fixed to the inlet 45. The supporter may connect a secondary fan device and the inlet 45. For example, inlet 45 may generate a supplemental air flow to increase air flow into humidifying assembly 40, or air from fan 32 may bypass humidifying assembly 40 with air flow within humidifying assembly 40 being entirely generated by inlet 45.

A second portion of air blown by the fan 32 may bypass the inlet 45 and may flow upward through a space between the outer case 16 (see FIG. 3) and the inner case 17 to pass through the inner grill 59 without passing through humidifying assembly 40. The air having passed through the inner grill 59 may flow upward to be discharged through the discharge port 12.

Figure 6:
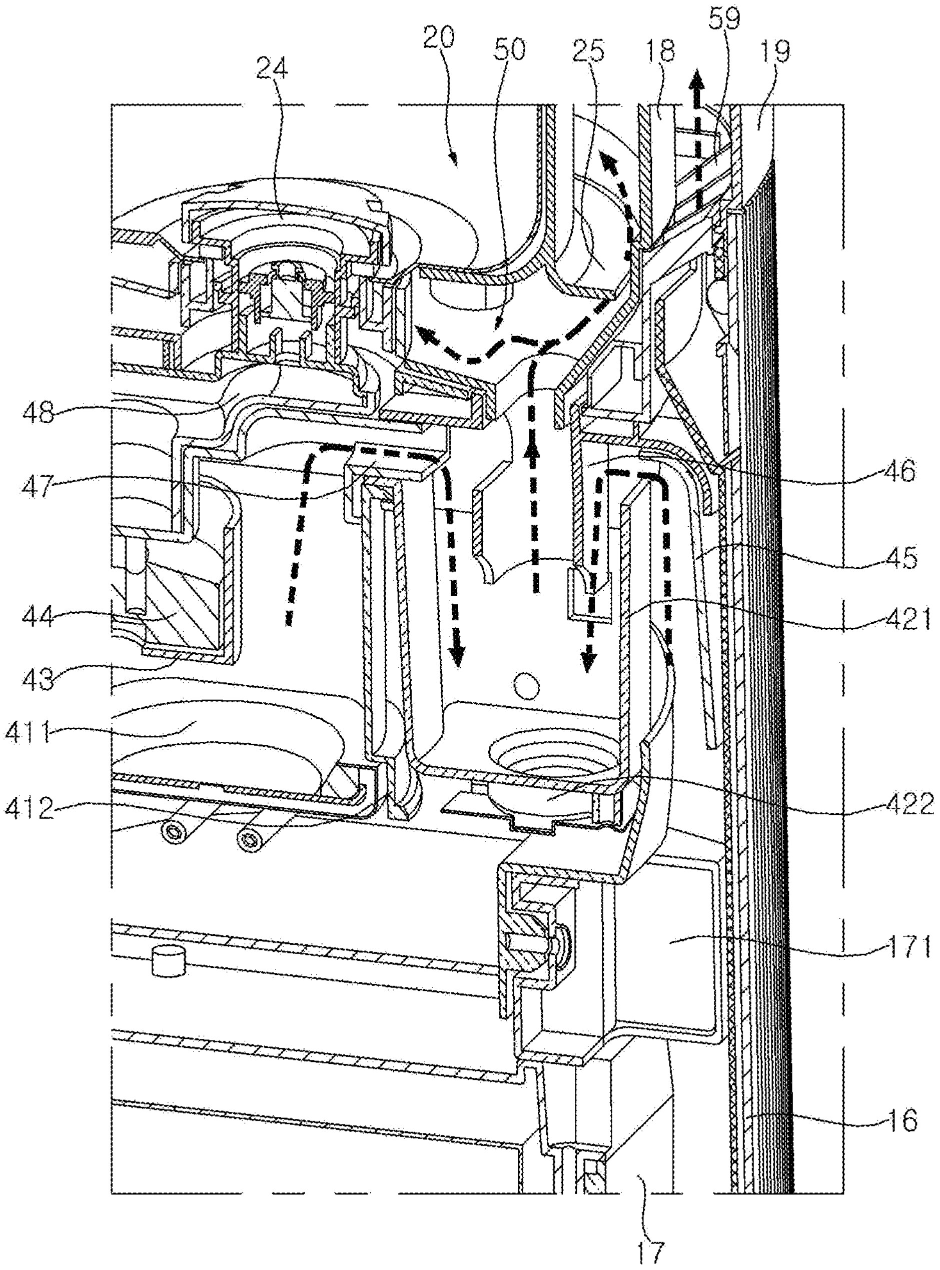
FIG. 6 is a cutaway view of a portion of a humidifier according to an embodiment.

Referring to FIG. 6, aspects of the humidifier 1 will be described below. FIG. 6 is an oblique, vertical cutaway view of a portion of the humidifier 1 according to certain implementations.

As previously described, a portion of air flowing upward between the outer case 16 and the inner case 17 may be introduced into the inlet 45. The guide 171 may be provided below vertically face a lower region of the inlet 45.

The air introduced into the humidifying chamber 421 through the inlet 45 may be mixed with the water droplets generated by driving the ultrasonic vibrator 422. The humidified air, mixed with the water droplets, may then flow upward through the outlet 46.

The humidifying chamber 421 may communicate with the heating chamber 411. For example, the connector 47 provided at upper regions of humidifying chamber 421 and the heating chamber 411 may connect the humidifying chamber 421 and the heating chamber 411. As previously described, the connection pipe 49 may also connect the heating chamber 411 and the humidifying chamber 421, and the connection pipe 49 may be provided below the connector 47 to allow heated water from the heating chamber 411 to flow into the humidifying chamber 421.

The air in the heating chamber 411 may be mixed with the air introduced into the humidifying chamber 421 to be discharged through the outlet 46. A portion of water introduced into the heating chamber 411 may be evaporated to be introduced in the form of water vapor into the humidifying chamber 421. The water vapor generated in the heating chamber 411 may be mixed with the humidified air carrying atomized water in the humidifying chamber 421 to be discharged through the outlet 46.

The air flowing upward from the humidifying chamber 421 through the outlet 46 may be introduced between the water tank 20 and the inner case 18. The humidified air discharged through the outlet 46 may flow upward between the water tank 20 and the inner case 18.

The humidifier 1 may include an inner cover 50. The inner cover 50 may be connected to the outlet 46. The inner cover 50 may be disposed between the water tank 20 and the humidifying assembly 40. For example, the air flowing through the outlet 46 may flow upward from the inner cover 50.

The water tank 20 may include a guide rim 25. The guide rim 25 may extend annularly along the circumference of the water tank 20. The guide rim 25 may be spaced above the outlet 46. The air flowing through the outlet 46 may be diffused by the guide rim 25 in a circumferential direction of the water tank 20. The humidified air diffused in the circumferential direction of the water tank 20 or otherwise guided may flow upward between the water tank 20 and the inner case 18.

At least a portion of the air flowing between the outer case 16 and the inner case 17 may flow upward through the inner grill 59. The inner grill 59 may be disposed between the outer case 19 and the inner case 18. The air having passed through the inner grill 59 may flow upward between the outer case 19 and the inner case 18.

Figure 7:
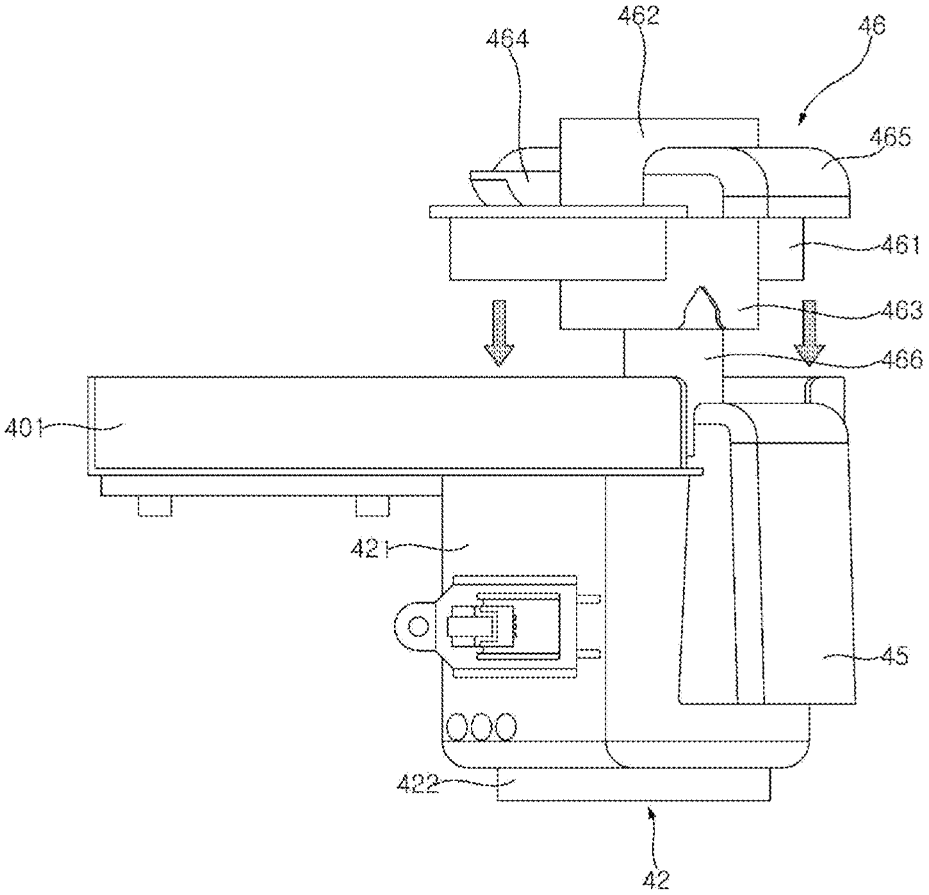
FIG. 7 is a diagram illustrating a portion of a humidifier according to an embodiment.

Referring to FIG. 7, aspects of the humidifier 1 will be described below. FIG. 7 is a diagram illustrating a portion of the humidifying assembly 40 in certain implementations.

As previously described, the humidifying assembly 40 may include the humidifying device 42. The humidifying device 42 may generate mist. The humidifying device 42 may include the humidifying chamber 42 and the ultrasonic vibrator 422.

The humidifying assembly 40 may include a body (or frame) 401. The body 401 may have a cylindrical shape with an open top. The heating device 41 (see FIG. 4) and the humidifying device 42 may be coupled to the body 401. The heating device 41 (see FIG. 4) and the humidifying device 42 may be coupled to a lower side of the body 401.

The humidifying assembly 40 may include the outlet 46. The air introduced into the humidifying device 42 through the inlet 45 may flow to the outlet 46 while containing atomized water droplets to form a mist. The outlet 46 may be coupled to the body 401. The outlet 46 may be coupled to an upper portion of the humidifying device 42.

The outlet 46 may include an outlet body 461. The outlet body 461 may be coupled to the body 401. For example, a portion of the outlet body 461 may be inserted into the humidifying chamber 421.

The outlet 46 may include a mist outlet port 462. The mist outlet port 462 may protrude upward from the outlet body 461. The mist generated in the humidifying device 42 may flow upward through the mist outlet port 462.

The outlet 46 may include a mist inlet port 463. The mist inlet port 463 may protrude downward from the outlet body 461. The mist inlet port 463 may extend toward the inside of the humidifying chamber 421. The mist generated in the humidifying device 42 may flow toward the mist outlet port 462 through the mist inlet port 463.

The outlet 4 may include a connector coupling part (or connector cover) 464. The connector coupling part 464 may extend toward the heating device 41 (see FIG. 4). The connector coupling part 464 may be coupled to the connector 47 (see FIG. 4).

The outlet 46 may include an inlet cover 465. The inlet cover 465 may be disposed above the inlet 45. The inlet cover 465 may cover an upper portion of the inlet 45.

The outlet 46 may include a supporter (or supporter wall) 466. The supporter 466 may extend downward from the outlet body 461. At least a portion of the supporter 466 may be disposed in the humidifying chamber 421. The supporter 466 may face a side wall of the humidifying chamber 421.

Figure 8:
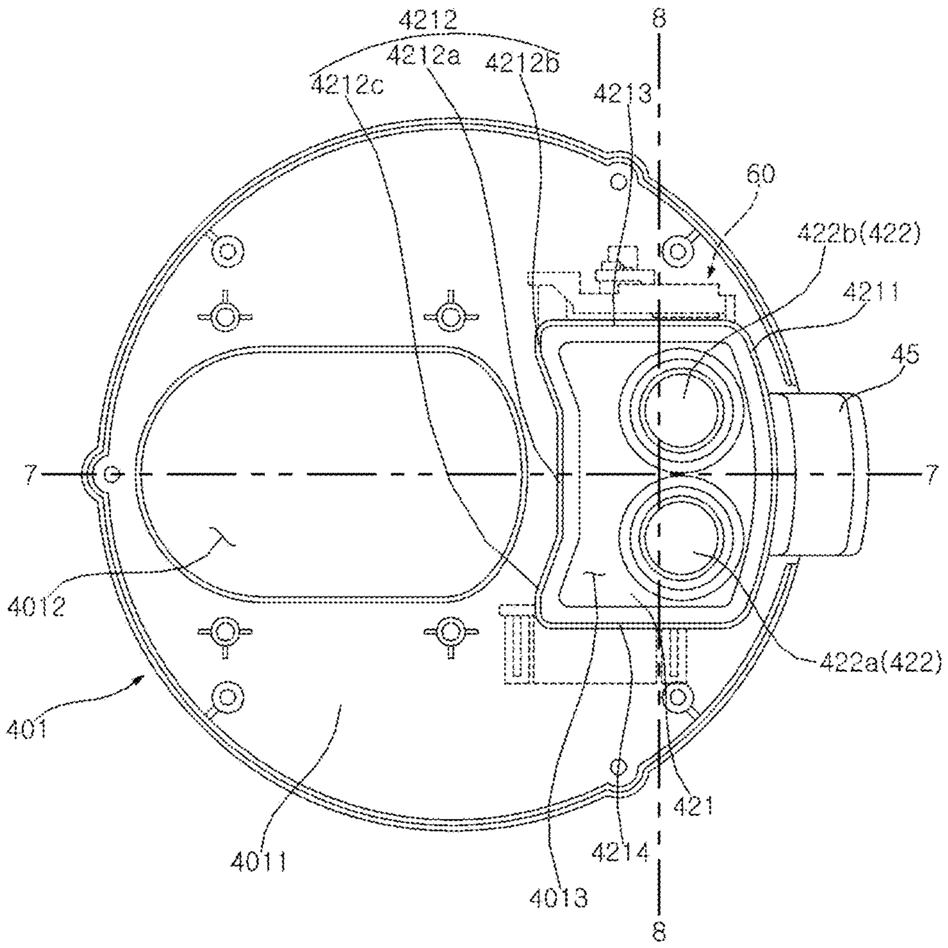
FIG. 8 is a diagram illustrating a portion of a humidifier according to an embodiment.

Referring to FIG. 8, aspects of the humidifier 1 will be described below. FIG. 8 is a diagram illustrating a portion of the humidifying assembly 40 as viewed from above in certain implementations.

The body 401 may include a body plate 4011. The body plate 4011 may have a substantially circular plate shape or other shape to be received within the outer case 16. The humidifying device 42 may be coupled to the body plate 4011.

The body 401 may include a first opening 4012. The first opening 4012 may be formed in the body plate 4011. The heating device 41 (see FIG. 6) may be coupled to the first opening 4012.

The body 401 may include a second opening 4013. The second opening 4013 may be formed in the body plate 4011. The humidifying device 42 may be coupled to the second opening 4013. The outlet 46 (see FIG. 4) may be inserted into the humidifying chamber 421 through the second opening 4013.

The internal space of the humidifying chamber 421 may communicate with the second opening 4013. There may be a plurality of ultrasonic vibrators 422.

The humidifying chamber 421 may include an outer wall 4211. The outer wall 4211 may be coupled to the inlet 45.

The humidifying chamber 421 may include an inner wall 4212. The inner wall 4212 may be spaced apart from the outer wall 4211. The internal space of the humidifying chamber 421 may be formed between the outer wall 4211 and the inner wall 4212. The inner wall 4212 may be disposed between the first opening 4012 and the outer wall 4211.

The inner wall 4212 may include a wall surface portion 4212*a*. The wall surface portion 4212*a* may face the outer wall 4211. The inner wall 4212 may include a first corner portion 4212*b*. The first corner portion 4212*b* may extend outside of the wall surface portion 4212*a*. The first corner portion 4212*b* may be curved toward the center of the body 401. The inner wall 4212 may include a second corner portion 4212*c*. The second corner portion 4212*c* may extend outside of the wall surface portion 4212*a*. The second corner portion 4212*c* may be curved toward the center of the body 401. The wall surface portion 4212*a* may be disposed between the first corner portion 4212*b* and the second corner portion 4212*c*.

The humidifying chamber 421 may include a first side wall 4213. The first side wall 4213 may connect the outer wall 4211 and the inner wall 4212. The first side wall 4213 may be connected to the first corner portion 4212*b*. The humidifying chamber 421 may include a second side wall 4214. The second side wall 4214 may connect the outer wall 4211 and the inner wall 4212. The second side wall 4214 may be connected to the second corner portion 4212*c*. The first side wall 4213 and the second side wall 4214 may be spaced apart from each other. The internal space of the humidifying chamber 421 may be formed between the first side wall 4213 and the second side wall 4214.

The humidifier 1 may include a sterilizer 60. The sterilizer 60 may be disposed in the humidifying device 42. In one example, the sterilizer 60 may emit ultraviolet light toward the humidifying chamber 421. In another example, the sterilizer 60 may generate a sterilizing substance, such as ozone or ions (e.g., silver or copper ions) introduced into the humidifying chamber 421.

Figure 9:
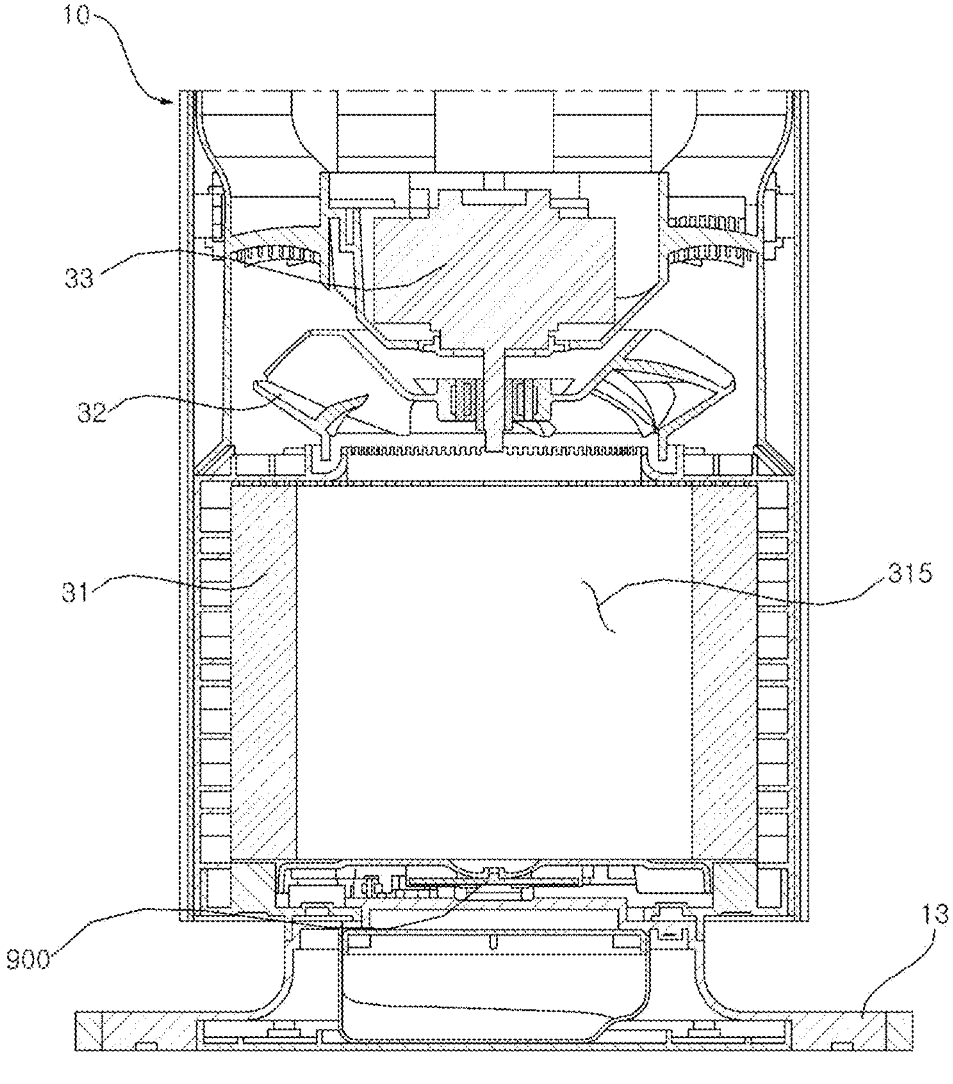
FIG. 9 is a diagram referred to in the description of a sterilization module mounted at a lower portion of a humidifier according to an embodiment.

According to an embodiment of the present disclosure, the humidifier 1 may include a sterilization module 900 (see FIG. 9) mounted at a lower portion thereof, such as above base 13 to face a portion of filter 31. FIG. 9 is a diagram illustrating aspects of the sterilization module 900 mounted at a lower portion of humidifier 1 according to an embodiment, and FIG. 10 is a diagram illustrating aspects of a base cover 1000 of humidifier 1 according to an embodiment.

Figure 10:
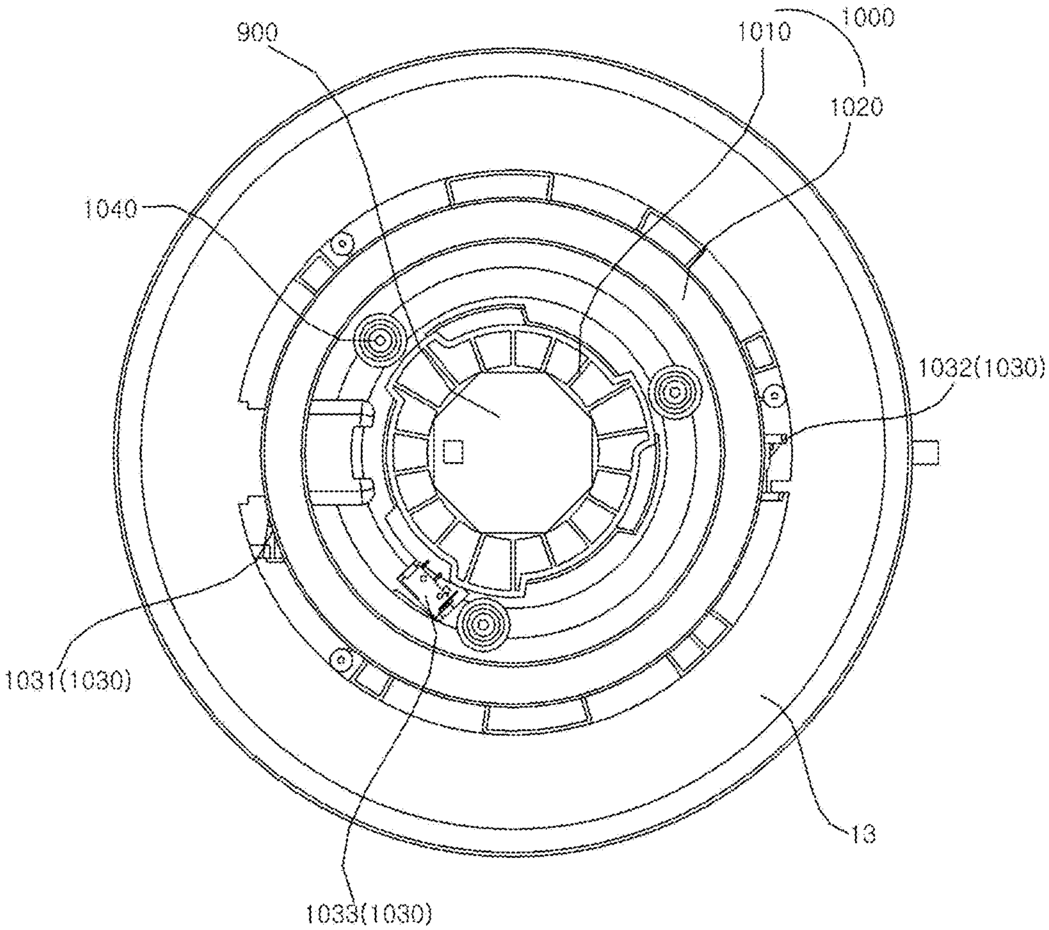
FIG. 10 is a diagram referred to in the description of a base cover of a humidifier according to an embodiment.

Referring to FIGS. 9 and 10, the humidifier 1 includes the case 10, the base 13 disposed below the case 10, and the filter 31 disposed in the case 10. The filter 31 may be disposed below the aforementioned humidifying assembly 40. The filter 31 may have a substantially cylindrical or other shape to be positioned within case 10.

The base 13 may form at least a portion of a lower surface of the humidifier 1, and may be placed on the floor of an indoor space and the like. A lower surface of the base 13 may have a substantially circular or other plate shape.

The filter 31 may include an inner hollow 315 formed by vertically penetrating through the filter 31. Suctioned air may be purified while flowing from an outer circumferential surface to an inner circumferential surface of the filter 31 and may flow upward from the filter 31 through the inner hollow 315. For example, air may flow from the inner hollow 315 and toward fan 32.

In addition, the humidifier 1 may include a base cover 1000 which is disposed above the base 13, and to which the case 10 is removably coupled. The sterilization module 900 may be disposed on or close to the base cover 1000 and may emit ultraviolet light to the inner hollow 315 of the filter 31 disposed at an upper side of the sterilization module 900, thereby sterilizing the filter 31 and the inner hollow 315. Additionally or alternatively, the sterilization module 900 may generate a sterilizing substance, such as ozone or ions (e.g., silver or copper ions) introduced into the inner hollow 315.

As previously described, the fan 32 may be disposed at an upper side of the filter 31 and may cause air, introduced from a circumferential surface of the filter 31, to flow upward from the filter 31. The fan motor 33 may be disposed at an upper side of or otherwise coupled to the fan 32 and may provide a force to rotate the fan 32.

The sterilization module 900 may emit ultraviolet light toward the inner hollow 315 of the filter 31 and may sterilize the filter 31 and the inner hollow 315. The sterilization module 900 may further emit ultraviolet light through the inner hollow 315 and toward the fan 32 disposed above the inner hollow 315, such as through openings in a lower surface of fan housing 321 (see FIG. 5).

When the case 10 is coupled to the base cover 1000 and the filter 31 is seated, the sterilization module 900 may emit ultraviolet light to the inner hollow 315 of the filter. In addition, if the case 10 is removed from or otherwise not coupled to the base cover 1000 or if the filter 31 is not seated, the sterilization module 900 may not emit ultraviolet light to the inner hollow 315 of the filter, such as to prevent the potentially harmful UV light from being emitted out of the case 10. Further, while emitting ultraviolet light, if the case 10 is separated from the base cover 1000 or the filter 31 is removed, the sterilization module 900 may stop emitting ultraviolet light. Accordingly, it is possible to prevent safety accident that may occur when a user's eyes are inadvertently exposed to ultraviolet light.

The base cover 1000 may be provided with one or more sensors to detect whether the case 10 is coupled to base cover 100 and whether the filter 31 is properly seated within the filter mounting space 311. For example, the base cover 1000 may include buttons 1030. When the case 10 is coupled and the filter 31 is seated, the buttons 1030 may be pressed, and the controller 34 may determine that the base 10 is coupled and the filter 31 is seated. Upon determining that the case 10 is coupled to the base cover 1000 and the filter 31 is seated based on the operation of the buttons 1030, the controller 34 may control the sterilization module 900 to emit ultraviolet light to the inner hollow 315 of the filter 31. Alternatively, when at least one of the buttons 1030 is not pressed, controller 34 may determine that either the base 10 is not coupled or the filter 31 is properly seated, and the controller 34 may control the sterilization module 900 to not emit the ultraviolet light.

The case 10 may include a first case 1101 (see FIG. 11) removably coupled to the base cover 1000, and a second case 1102 (see FIG. 12) opposite to the first case 1101 with respect to the base cover 1000 and removably coupled to the base cover 1000. The first case 1101 and the second case 1102 may be respectively coupled to the base cover 1000. If at least one of the first case 1101 and the second case 1102 is separated from the base cover 1000, the sterilization module 900 may stop emitting ultraviolet light.

The base cover 1000 may include a first button 1031 which operates when the first case 1101 is coupled to the base cover 1000, and a second button 1032 which operates when the second case 1102 is coupled to the base cover 1000. For example, if the first and second cases 1101 and 1102 are respectively coupled to the base cover 1000, the first and second buttons 1031 and 1032 may be turned on (e.g., pressed down), and if not, the first and second buttons 1031 and 1032 may be turned off (e.g., not pressed down).

The first case 1101 may include a first rib 1110 protruding from an inner surface of the first case 1101 and configured to contact and press the first button 1031 when coupled to the base cover 1000. In addition, the second case 1102 may include a second rib 1120 protruding from an inner surface of the second case 1102 and configured to make contact with and press the second button 1032 when coupled to the base cover 1000.

Figure 11:
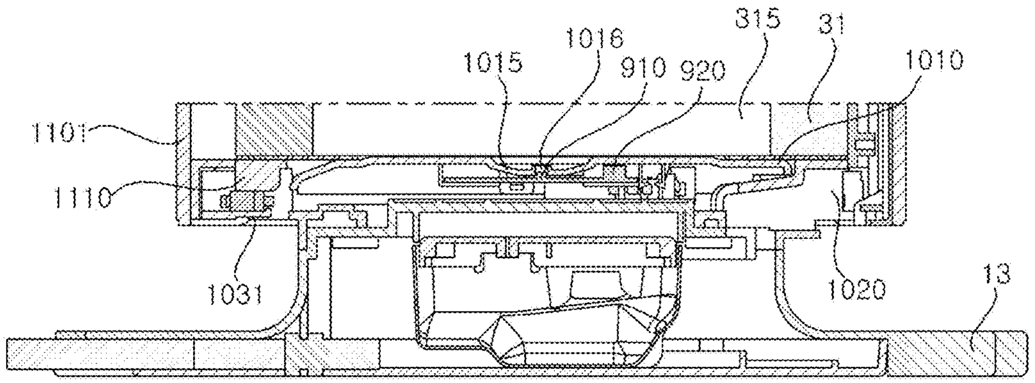
FIGS. 11 and 12 are diagrams of a case of a humidifier and a base cover which are coupled to each other, according to an embodiment.
Figure 12:
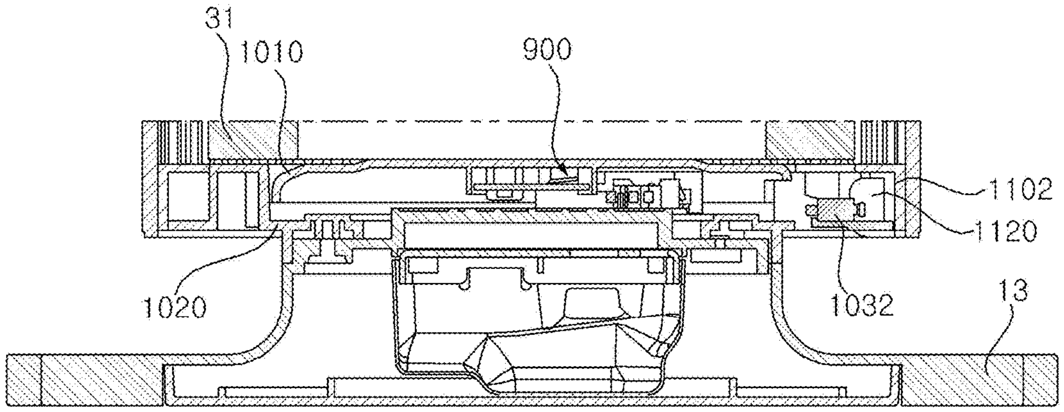

FIGS. 11 and 12 are diagrams illustrating aspects of humidifier 10 and base cover 1000 when coupled to each other, according to an embodiment. Referring to FIG. 11, when the first case 1101 is coupled to the base cover 1000, the first rib 1110 protruding from the first case 1101 may press the first button 1031. When the first button 1031 is pressed, a signal corresponding thereto may be transmitted from the first button 1031 to the controller 34. Alternatively, the first button 1031 may send a signal to the controller 34 indicating when the first button 1031 is not pressed. Accordingly, the controller 34 may determine whether the first case 1101 is coupled to the base cover 1000 and may control the operation of the sterilization module 900.

Referring to FIG. 12, when the second case 1102 is coupled to the base cover 1000, the second rib 1120 protruding from the second case 1102 may press the second button 1032. When the second button 1032 is pressed, a signal corresponding thereto may be transmitted from the second button 1032 to the controller 34. Alternatively, the second button 1032 may send a signal to the controller 34 indicating when the first button 1032 is not pressed. Accordingly, the controller 34 may determine whether the second case 1102 is coupled to the base cover 1000 and may control the operation of the sterilization module 900.

The base cover 1000 may include a filter cover 1010 that may contact a lower surface of the filter 31, and a cover body 1020 that may be coupled to a lower part of the filter cover 1010. The filter cover 1010 may form a portion of an upper surface of the base cover 1000. The filter cover 1010 may form an upper surface of a central portion of the base cover 1000, and the cover body 1020 may be disposed on a side surface and a lower portion of the filter cover 1010.

The sterilization module 900 may be disposed between the filter cover 1010 and the cover body 1020. In addition, the sterilization module 900 may be coupled to the filter cover 1010.

The sterilization module 900 may include a board 920 and a light source 910 mounted on the board 920. The board 920 may be mounted on a lower surface of the filter cover 1010. The board 920 may be referred to as a substrate. For example, the board 920 may be a printed circuit board (PCB). The light source 910 may provide light in an ultraviolet wavelength range. For example, the light source 910 may be an UVC LED or a UVC lamp providing light in a wavelength range of 100 nm to 280 nm. Accordingly, light from the light source 910 may sterilize bacteria or microbes present in the fan 32. Further, light from the light source 910 may sterilize bacteria or microbes present in the filter 31 or contained in air having passed through the filter 31.

The filter cover 1010 and the cover body 1020 may be coupled to each other via a plurality of coupling parts 1040 with a fastening member (or coupler) 1045 such as a screw, bolt, or the like. For example, a screw thread may be formed on an inner circumferential surface of each of the plurality of coupling parts 1040, and each of a plurality of fastening members 1045 may be a screw fastened to the inner circumferential surface thereof.

Referring to FIG. 11, the filter cover 1010 may include a recessed portion (or region) 1015 that is recessed downward from an upper surface thereof, and a hole 1016, through which the ultraviolet light passes, may be formed at the center of the recessed portion 1015. Thus, UV light may pass through hole 1016 and into inner hollow 315.

Figure 13:
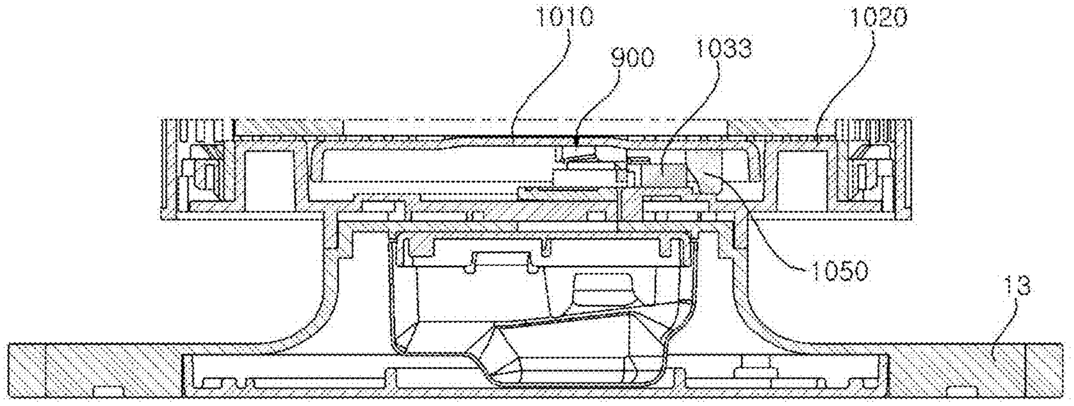
FIGS. 13, 14A, and 14B are diagrams related seating of a filter of a humidifier according to an embodiment.
Figure 14A:
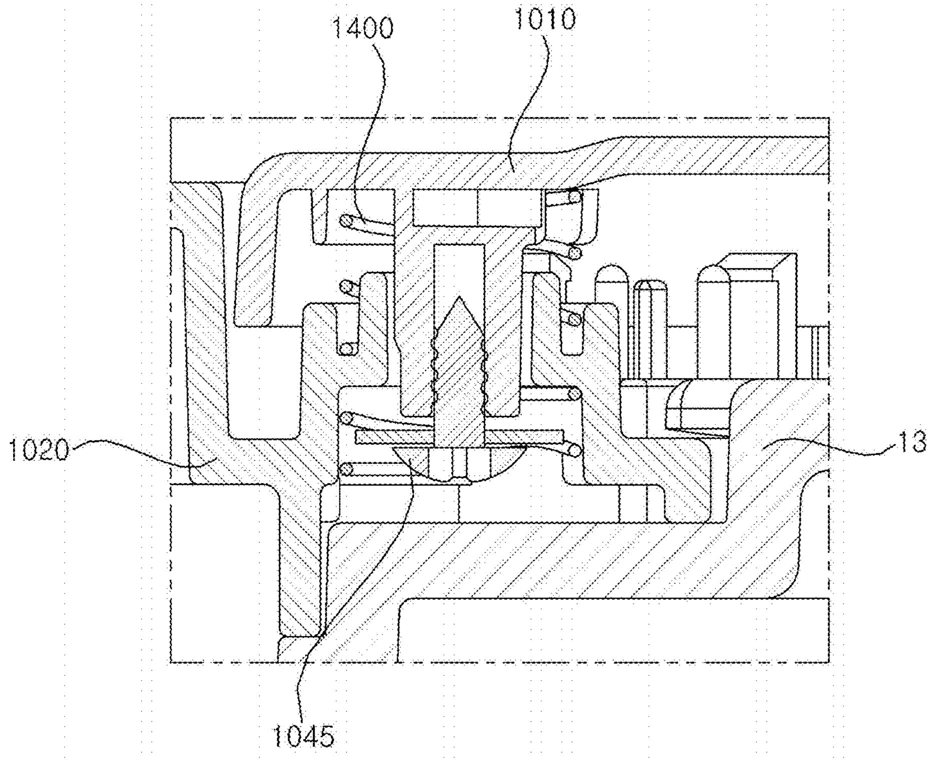
Figure 14B:
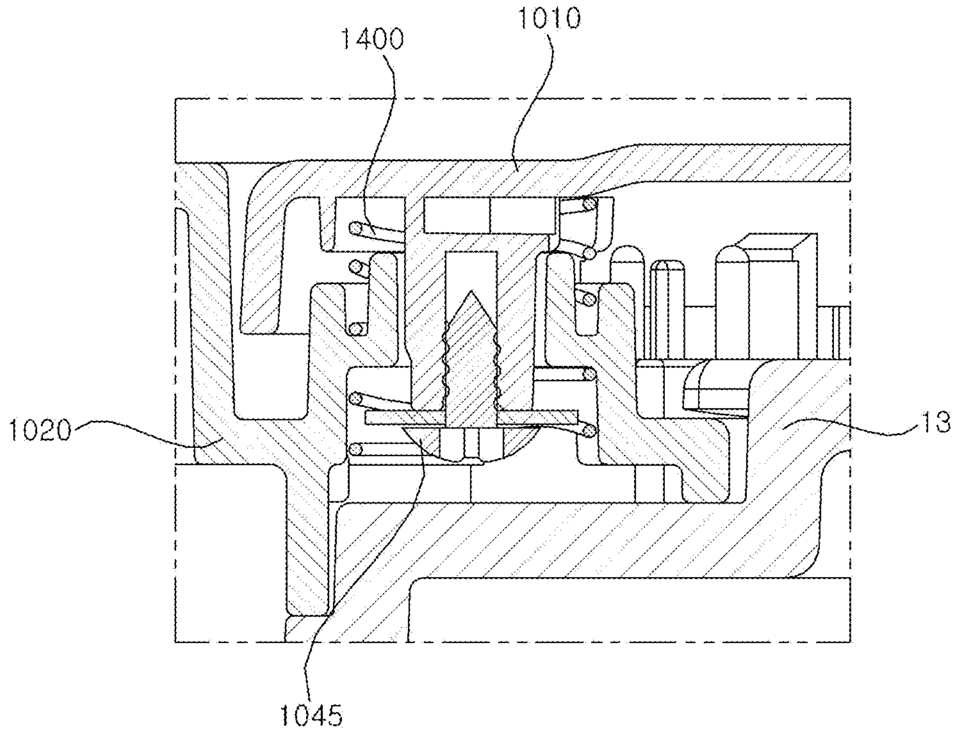

FIGS. 13, 14A, and 14B are diagrams depicting aspects of seating filter 31 of humidifier 1 according to an embodiment. FIG. 13 illustrates contact between a third rib 1050 and a third button 1033 when the filter 31 is seated, and FIG. 14A illustrates a state in which the filter 31 is not seated, and FIG. 14B illustrates a state in which the filter 31 is seated.

Referring to FIGS. 13, 14A, and 14B, the base cover 1000 may further include an elastic member 1400 connected to the filter cover 1010 and the cover body 1020. In addition, the filter cover 1010 may include a third rib 1050 protruding in a downwards direction, toward base 13. The cover body 1020 may include a third button 1033 that may contact the third rib 1050 due to the elastic member 1400 being compressed when the filter 31 is seated on the filter cover 1010. For example, if the filter 31 is seated on the filter cover 1010, the third button 1033 may be turned on, and if not, the third button 1033 may be turned off. Alternatively, the third button 1033 may be turned on when the filter 31 is not seated on the filter cover 1010, and the third button 1033 may be turned off when the filter 31 is seated on the filter cover 1010.

The elastic member 1400 may have elasticity to provide an elastic force when compressed. The elastic member 1400 may be disposed between the filter cover 1010 and the cover body 1020 and may be fixed to the filter cover 1010 and the cover body 1020. For example, the elastic member 1400 may be a spring and may be wound around an outer circumferential surface of each of the plurality of coupling parts 1040. The elastic member 1400 may be disposed outside of the fastening members 1045 of the coupling parts 1040. The elastic member 1400 may be in contact with the filter cover 1010 and the cover body 1020, or may be in contact with at least the cover 1020 so as to be compressed when the filter 31 is seated.

If no load is applied to the filter cover 1010 (e.g., the filter 31 is not seated), the elastic member 1400 may be elastically restored, and the filter cover 1010 may be moved upward and away from the cover body 1020 due to force applied by elastic member 1400. Referring to FIG. 14A, when the filter 31 is not seated, the filter cover 1010 is lifted by elastically restoration of the elastic member 1400. Referring to FIG. 14B, when the filter 31 is seated, the elastic member 1400 is compressed such that the filter cover 1010 is lowered.

When the filter 31 is seated on the filter cover 1010, the elastic member 1400 may be compressed such that the filter cover 1010 is lowered. As previously described, as the filter cover 1010 is lowered, the third rib 1050 that protrudes downward from the filter cover 1010 may press the third button 1033. When the third button 1033 is pressed, a signal corresponding thereto is transmitted from the third button 1033 to the controller 34. Accordingly, the controller 34 may determine whether the filter 31 is seated and may control the operation of the sterilization module 900. For example, when the third button 1033 is separated from the third rib 1050, the controller 34 may instruct the sterilization module 900 to deactivate light source 910 and stop emitting the ultraviolet light.

The humidifier 1 according to an embodiment of the present disclosure includes the sterilization module 900 mounted at a lower portion thereof, and the sterilization module 900 operates only when all the first to third buttons 1031, 1032, and 1033 are pressed. Accordingly, when a user removes the filter 31 or cleans the inside of the humidifier, it is possible to prevent the user's eyes from being exposed to the ultraviolet light emitted by the sterilization module 900.

For example, if all the first to third buttons 1031, 1032, and 1033 are in an on (pressed) state, the controller 34 may operate the light source 910. For example, as previously described, when the filter 31 is seated on the base cover 1000, and the first case 1101 and the second case 1102 are coupled to the base cover 1000, the controller 34 may operate the light source 910.

Accordingly, when the light from the light source 910 may be prevented from leaking to the outside of the filter 31 and the case 10, the controller 34 may operate the light source 910 to sterilize the fan 32. For example, when the filter 31 or the case 10 is separated from the humidifier 1, the controller may stop the operation of the light source 910 to fundamentally block UV light from leaking to the outside of humidifier 1.

Figure 15:
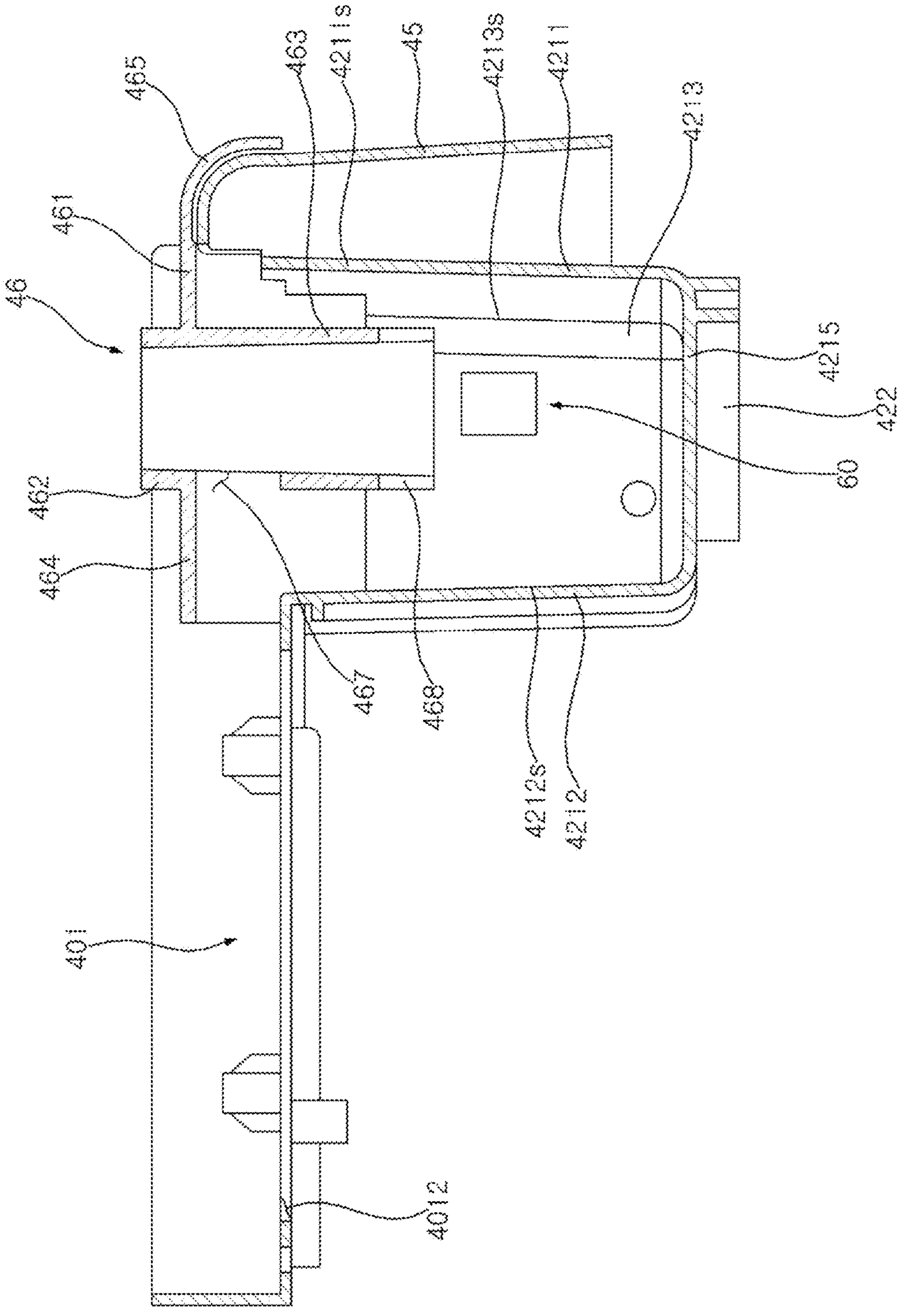
FIG. 15 is a cross-sectional view of a portion of a humidifier according to an embodiment.

FIG. 15 is a cross-sectional view of a portion of the humidifier 1 including sterilizer 60 according to an embodiment and, more specifically, depicts aspects of a vertical cross-sectional view of a portion of the humidifying assembly 40 taken along line 7-7 of FIG. 8 in certain implementations.

As described above with reference to FIG. 8, the humidifying assembly 40 may include the humidifying chamber 421 defining a space in which storing is contained, and the sterilizer 60 that emits sterilizing ultraviolet light into the humidifying chamber 421, so as to sterilize the into the humidifying chamber 421 and water remaining in the humidifying chamber 421.

In addition, the humidifying assembly 40 may include reflection plates 4211*s*, 4212*s*, 4213*s*, and 4214*s* (see FIGS. 15 and 16) arranged along a circumferential wall of the humidifying chamber 421, to emit ultraviolet light into the humidifying chamber 421 so that there is no shadow area. The reflection plates 4211*s*, 4212*s*, 4213*s*, and 4214*s* may be spaced apart from the sterilizer 60 and disposed to face the sterilizer 60. Referring to FIG. 15, the sterilizer 60 may be disposed on a first side wall 4213. The sterilizer 60 may be disposed between an outer wall 4211 and an inner wall 4212.

The humidifying chamber 421 may include a lower chamber wall 4215. The lower chamber wall 4215 may be coupled to the vibrator 422 that atomizes water to form suspended droplets. The vibrator 422 may be disposed under or near the lower chamber wall 4215.

The sterilizer 60 may be disposed between the outlet 46 and the lower chamber wall 4215. The sterilizer 60 may be disposed below the outlet 46. The outlet 46 may include a mist inlet port 463. The mist inlet port 463 may extend to the inside of the humidifying chamber 421.

The outlet 46 may include a communication port 467. The communication port 467 may face the connector coupling part 464. The communication port 467 may be opened to the mist inlet port 463. The outlet 46 may also include a lower outlet end 468. The lower outlet end 468 may be positioned inside the humidifying chamber 421. The sterilizer 60 may be disposed below the lower outlet end 468. The sterilizer 60 may be disposed above the lower chamber wall 4215.

The humidifying assembly 40 may include the reflection plates 4211*s*, 4212*s*, 4213*s*, and 4214*s*. The reflection plates 4211*s*, 4212*s*, 4213*s*, and 4214*s* may face an internal space of the humidifying chamber 421. The reflection plates 4211*s*, 4212*s*, 4213*s*, and 4214*s* may be disposed on side walls 4211, 4212, 4213, and 4214 of the humidifying chamber 421. Light emitted by the sterilizer 60 may reach at least one of the reflection plates 4211*s*, 4212*s*, 4213*s*, and 4214*s* to be reflected therefrom.

The reflection plates 4211*s*, 4212*s*, 4213*s*, and 4214*s* may include an outer reflection plate 4211*s*. The outer reflection plate 4211*s* may be disposed on the outer wall 4211. The outer reflection plate 4211*s* may be coupled to a surface of the outer wall 4211 that faces the internal space of the humidifying chamber 421.

The reflection plates 4211*s*, 4212*s*, 4213*s*, and 4214*s* may include an inner reflection plate 4212*s*. The inner reflection plate 4212*s* may be disposed on the inner wall 4212. The inner reflection plate 4212*s* may be coupled to a surface of the inner wall 4212 that faces the internal space of the humidifying chamber 421.

The reflection plates 4211*s*, 4212*s*, 4213*s*, and 4214*s* may include a first lateral reflection plate 4213*s*. The first lateral reflection plate 4213*s* may be disposed on the first side wall 4213. The first lateral reflection plate 4213*s* may be coupled to a surface of the first side wall 4213 that faces the internal space of the humidifying chamber 421.

Figure 16:
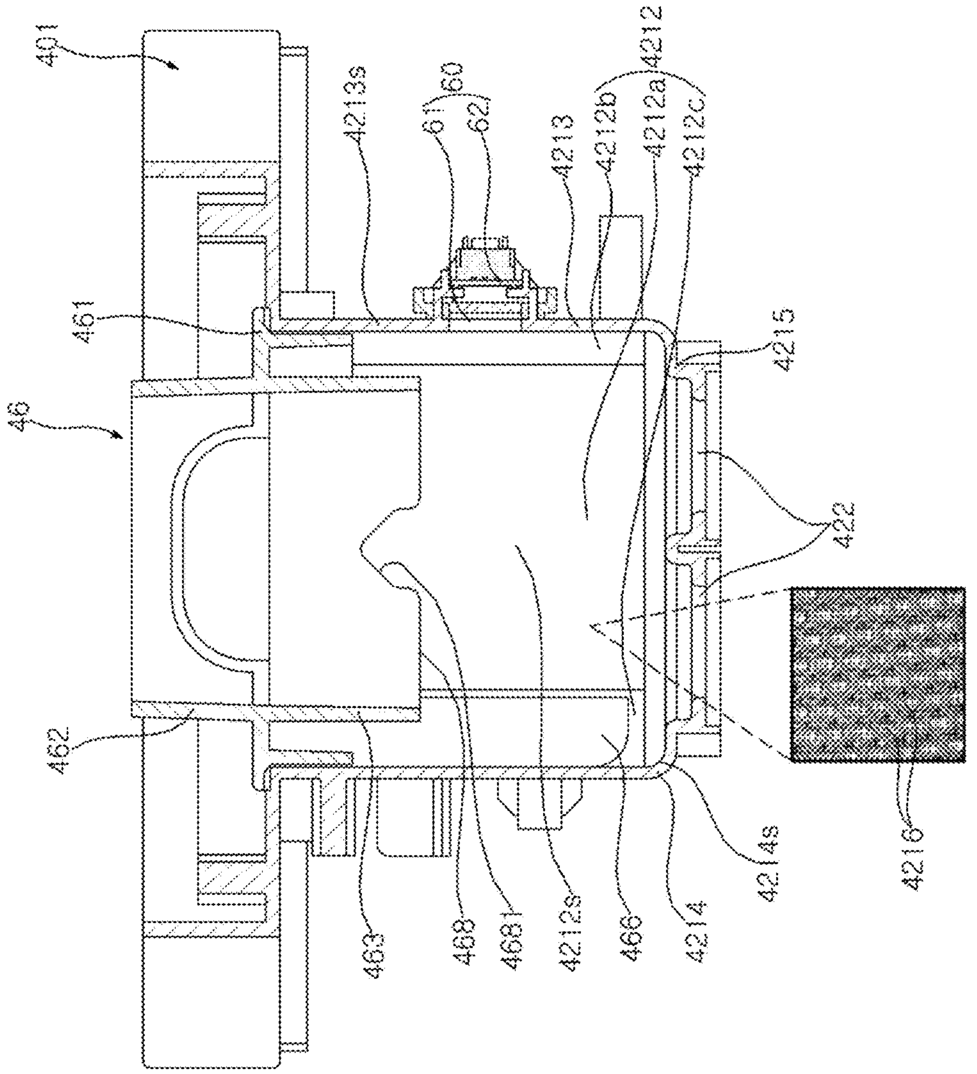
FIG. 16 is a cross-sectional view of a portion of a humidifier according to an embodiment.

The reflection plates 4211*s*, 4212*s*, 4213*s*, and 4214*s* may include a second lateral reflection plate 4214*s* (see FIG. 16). The second lateral reflection plate 4214*s* may be disposed on the second side wall 4214. The second lateral reflection plate 4214*s* may be coupled to a surface of the second side wall 4214 that faces the internal space of the humidifying chamber 421.

FIG. 16 is a cross-sectional view of a portion of humidifier 1 according to an embodiment, and depicts aspects of a vertical cutaway view of a portion of the humidifying assembly 40 taken along line 8-8 of FIG. 8 in certain implementations.

Referring to FIG. 16, the sterilizer 60 may be disposed on the first side wall 4213. The sterilizer 60 may emit light to the internal space of the humidifying chamber 421.

The outlet 46 may include a recess (or cutout) 4681. The recess 4681 may be formed at a lower end of the outlet 46. The recess 4681 may be recessed upward from the outlet 46. The sterilizer 60 may be disposed below the lower outlet end 468. The sterilizer 60 may be disposed below the recess 4681.

The sterilizer 60 may include a lamp (or light guide) 61. The sterilizer 60 may include a light emitter 62. The lamp (or light guide) 61 may be exposed to the internal space of the humidifying chamber 421. The lamp (or light guide) 61 may radiate ultraviolet light, generated by the light emitter 62, to the inside of the humidifying chamber 421. The light emitter 62 may be disposed outside of the humidifying chamber 421. The light emitter 62 may generate ultraviolet light toward the lamp (or light guide) 61.

A portion of the supporter 466 may extend into the humidifying chamber 421. The supporter 466 may extend along the second side wall 4214. The supporter 466 may be spaced apart from the first side wall 4213. The supporter 466 may face the sterilizer 60. The supporter 466 may partially cover the second side wall 4214. The supporter 466 may be made of an opaque material. However, the supporter 466 may be a transparent material and may also reflect ultraviolet light.

The second lateral reflection plate 4214*s* may be exposed on a lower side of the supporter 466. However, the second lateral reflection plate 4214*s* may also be coupled to one surface of the supporter 466. In this case, light emitted by the sterilizer 60 may be reflected on the second lateral reflection plate 4214*s*.

The supporter 466 may face the second corner portion 4212*c*. A portion of the supporter 466 may extend in a direction in which the second corner portion 4212*c* is curved. The first corner portion 4212*b* may be disposed between the mist inlet port 463 and the first side wall 4213.

At least one of the reflection plates 4211*s*, 4212*s*, 4213*s*, and 4214*s* may include dimples 4216. A plurality of dimples 4216 may be formed on one or more of reflection plates 4211*s*, 4212*s*, 4213*s*, and 4214*s*. The dimples 4216 may be recessed from the reflection plates 4211*s*, 4212*s*, 4213*s*, and 4214*s* in a direction away from the internal space of the humidifying chamber 421.

Ultraviolet light emitted by the sterilizer 60 may be reflected from the reflection plates 4211*s*, 4212*s*, 4213*s*, and 4214*s*, to be diffused uniformly into the humidifying chamber 421. In this case, the dimples 4216 may allow the ultraviolet light to be reflected at various angles, thereby facilitating UV light diffusion within the humidifying chamber 421.

In addition, if all the first to third buttons 1031, 1032, and 1033 are in an on state, the controller 34 may operate the sterilizer 60 disposed in the humidifying chamber 421. For example, when the filter 31 is seated on the base cover 1000, and the first case 1101 and the second case 1102 are coupled to the base cover 1000, the controller 34 may operate the sterilizer 60. Similarly, when any of the first to third buttons 1031, 1032, and 1033 is not pressed, the controller 34 may deactivated the sterilizer 60 disposed in the humidifying chamber 421. Accordingly, it is possible to prevent the sterilizer 60 from operating, for example, while the filter 31 is not properly seated or otherwise separated from the case 10.

Figure 17:
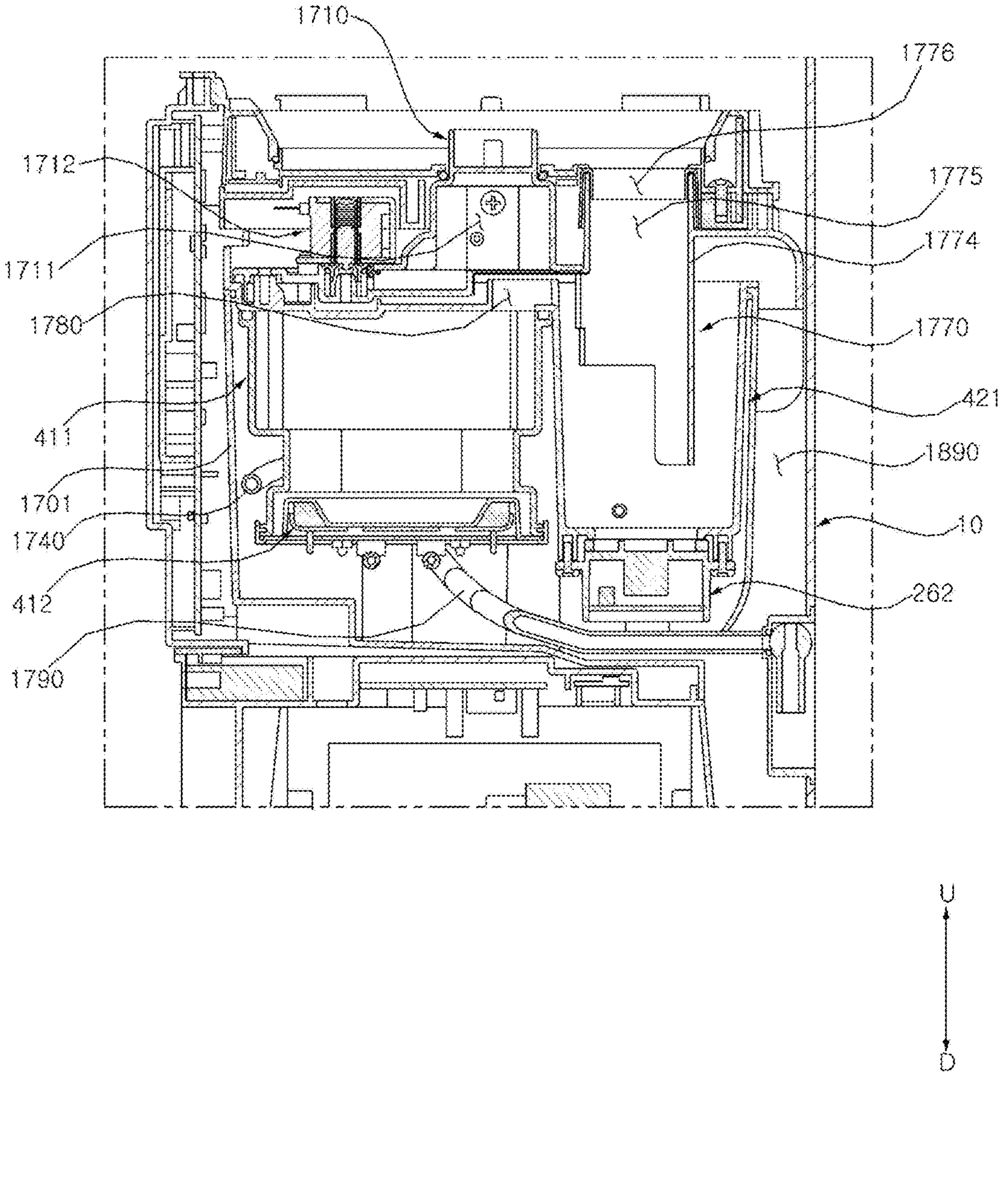
FIG. 17 is a longitudinal cross-sectional view of a humidifying assembly according to an embodiment.

FIG. 17 is a longitudinal cross-sectional view depicting aspects of the humidifying assembly 4—according to an embodiment.

As previously described, FIG. 4 illustrates an example of supplying water using a floating valve 44 and the structure of the humidifying assembly 40, but the present disclosure is not limited thereto. For example, the embodiments of the present disclosure may supply water by using a solenoid or other type of valve, and may also be applied to the humidifying assembly 40 having other structures.

Referring to FIG. 17, the humidifying assembly 40 may include a main housing 1701, a supply pipe 1710, a first valve 1712, the heating chamber 411, a first connection pipe 1740, a drain pipe 1790, the humidifying chamber 421, and a partition cover 1770.

The main housing 1701 may be disposed in the case 10. The main housing 1701 may accommodate the humidifying chamber 421 and the heating chamber 411, as will be described below. The main housing 1701 may have an open top.

The supply pipe 1710 may be a pipe through which water is supplied to the humidifying assembly 40. The supply pipe 1710 may be connected to the humidifying assembly 40. Water contained in the water tank 20 may be supplied to the humidifying assembly 40 through the supply pipe 1710. For example, the water stored in the water tank 20 may move to the heating chamber 411 through the supply pipe 1710. A supply chamber 1711 may be formed in the supply pipe 1710. The water introduced into the supply pipe 1710 may pass through the supply chamber 1711 to flow to the heating chamber. The water introduced into the supply pipe 1710 may be temporarily stored in the supply chamber 1711.

The first valve 1712 may control the flow of water supplied to the humidifying assembly 40 through the supply pipe 1710. For example, when the first valve 1712 is opened, the water stored in the supply chamber 1711 may move to the heating chamber 411. By contrast, if the first valve 1712 is closed, the supplied water may be temporarily stored in the supply chamber 1711. The first valve 1712 may be opened and closed in response to an electrical signal of the controller 34. The first valve 1712 may be activated and controlled by the controller 34. For example, the first valve 1712 may be a solenoid valve that is driven by a driving signal received from or managed by the controller 34. The first valve 1712 may be disposed above the heating chamber 411. The first valve 1712 may be disposed at the supply pipe 1710. For example, the first valve 1712 may be disposed between the heating chamber 411 and the supply pipe 1710. The first valve 1712 may be upwardly spaced apart from the heating chamber 411. For example, the first valve 1712 may be upwardly spaced apart from an upper surface of the heating chamber 411.

The heating chamber 411 may be disposed in the main housing 1701. The heating chamber 411 may heat the water introduced through the supply pipe 1710. The heating chamber 411 may heat and sterilize water. The sterilized water heated in the heating chamber 411 may flow to the humidifying chamber 421.

The first connection pipe 1740 may be a pipe through which water stored in the heating chamber 411 flows to the humidifying chamber 421. The first connection pipe 1740 may have a height that decreases toward a downstream side. For example, the first connection pipe 1740 may be inclined downwardly toward the downstream side. The first connection pipe 1740 may be formed of metal or other material having a high thermal conductivity. The water heated in the heating chamber 411 may decrease in temperature while flowing in the first connection pipe 1740 due to heat in the water being transferred to the first connection pipe 1740.

The drain pipe 1790 may be connected to the heating chamber 411. The drain pipe 1790 may discharge remaining water stored in the heating chamber 411. The remaining water may be discharged to the outside of the case 10 through the drain pipe 1790. The drain pipe 1790 may be connected to a lower part of the heating chamber 411. For example, the drain pipe 1790 may be connected to a bottom surface of the heating chamber 411.

The humidifying chamber 421 may generate humidified air by using the supplied water. The humidified air may refer to air containing mist and/or water vapor. The humidifying chamber 421 may generate humidified air using any one of an ultrasonic type, a heating type, an evaporative type, and a disk type method for forming water droplets. For example, the humidifying chamber 421 may generate humidified air by atomizing the supplied water using a vibrator 262.

The vibrator 262 may be disposed on a bottom surface of the humidifying chamber 421. The vibrator 262 may atomize water into fine droplets by using ultrasonic vibration. The vibrator 262 may correspond or include the ultrasonic vibrator 422 described above.

The partition cover 1770 may be disposed at an upper side of the main housing 1701. The partition cover 1770 may cover the upper part of the heating chamber 421. The partition cover 1770 may separate a passage for water to flow into the humidifying chamber 421 from a passage for water to be discharged from the humidifying chamber 421. For example, the partition cover 1770 may include an air supply pipe 1710 which is a passage through which a portion of upwardly flowing air, flowing in an internal air-blowing passage 1890, is introduced into the humidifying chamber 421, and a discharge pipe 1774 through which the portion of the upwardly flowing air introduced into the humidifying chamber 421 and mist remaining stagnant in the humidified chamber 421 are discharged together. The air supply pipe 1710 may connect the internal air-blowing passage 1890 and the humidifying chamber 421. The upwardly flowing air flowing into the humidifying chamber 421 may flow while pulling the mist generated in the humidifying chamber 421. In this manner, the mist generated in the humidifying chamber 421 may be discharged. The discharge pipe 1774 may extend in an up-down direction. The discharge pipe 1774 may form a discharge passage 1775. A humidified air discharge port 1776 may be formed at one end of the discharge pipe 1774. The discharge pipe 1774 may be inserted into the humidifying chamber 421.

The humidifying assembly 40 may include a communication passage 1780 connecting the heating chamber 411 and the humidifying chamber 421. The communication passage 1780 may connect an upper portion of the heating chamber 411 and an upper portion of the humidifying chamber 421. Water vapor may be generated when the heating chamber 411 heats the supplied water. The generated water vapor may flow to the humidifying chamber 421 through the communication passage 1780. The discharge pipe 1774 may be opened toward the communication passage 1780. The communication passage 1780 may be connected to the discharge passage 1775. The water vapor moving from the heating chamber 411 to the humidifying chamber 421 through the communication passage 1780 may be discharged through the discharge pipe 1774.

In this manner, the humidified air may contain the water vapor, generated in the heating chamber 411, the mist generated in the humidified chamber 421, and the upward air flow generated by the blower fan 32. The humidified air generated in the heating chamber 411 and the humidified air generated in the humidifying chamber 421 may be discharged together, such that pleasant, humidified air may be provided.

FIG. 18 is a schematic view of humidifier 1 according to an embodiment. Referring to FIG. 18, the humidifier 1 according to an embodiment includes the case 10, the water tank 20, the humidifying assembly 40, and the blower fan 32.

Indoor air (Fi) may be introduced through the inlet 11 formed in the case 10. The inlet 11 may be formed at a lower part of the case 10. The air (Fi) introduced into the case 10 may flow through a channel formed therein. The air (Fi) flowing in the case 10 may be discharged back into a room through the outlet 12 formed at an upper part of the case 10.

The water tank 20 may store water. The water tank 20 may include a water storage space 1810 in which water is contained. The water (Fs1) stored in the water storage space 1810 may be supplied to the humidifying assembly 40. The humidifying assembly 40 may generate humidified air by using the supplied water (Fs1).

The humidifying assembly 40 may generate humidified air. The humidified air may contain mist and/or water vapor. That is, the humidified air may refer to air containing mist and/or water vapor. The humidified air may have a higher humidity than the humidity of ambient air in a room.

The humidifying assembly 40 may include a heating chamber 411. The water (Fs1) supplied from the water tank 20 may be introduced into the heating chamber 411. The heating chamber 411 may heat the water (Fs1) supplied from the water tank 20. The heating chamber 411 may heat and sterilize the supplied water.

The humidifying assembly 40 may include the humidifying chamber 421. The water (Fs1) sterilized in the heating chamber 411 may move to the humidifying chamber 421. The humidifying chamber 421 may generate humidified air by using the water supplied from the heating chamber 411. The humidifying chamber 421 may generate humidified air by using any one of an ultrasonic type, a heating type, an evaporative type, and a disk type. For example, the humidifying chamber 421 may generate humidified air by atomizing the supplied water using an ultrasonic vibrator.

The blower fan 32 may be disposed in the case 10. The blower fan 32 may be disposed below the humidifying assembly 40. The blower fan 32 may generate a flow of air flowing in the case. The blower fan 32 may generate a flow of air (Fi) flowing from the inlet 11 toward the outlet. For example, the blower fan 32 may generate an upward flow of air flowing from the inlet 11, formed at a lower portion of the case 10, toward the outlet 12 formed in an upper surface of the case 10.

The case 10 may include an internal air-blowing passage 1890. The internal air-blowing passage 10 may be formed in the case 10. The internal air-blowing passage 1890 may be a passage through which air blown by the blower fan 32 flows. The air (Fi) introduced through the inlet 11 may flow toward the blower fan 32 through a suction passage 330. The air, having passed through the blower fan 32, may flow through the internal air-blowing passage 1890 (Fi).

The case 10 may include a discharge passage associated with the discharge port 12 (see FIG. 3). The discharge port 12 may be formed in the case 10. The air (Fd), having passed through the internal air-blowing passage 1890, may flow to a portion of the discharge port 12. The discharge port 12 may be disposed at an upper part of the internal air-blowing passage 1890. The discharge port 12 may be disposed on a downstream side of the internal air-blowing passage 1890.

The discharge port 12 may include a first discharge passage 1000*a* and a second discharge passage 1000*b*. The discharge port 12 may include a first discharge port 12*a* corresponding to the first discharge passage 1000*a* and a second discharge port 12*b* corresponding to the second discharge passage 1000*b*. The second discharge passage 1000*b* may be formed in the case 10. The first discharge passage 1000*a* may be formed radially within the second discharge passage 1000*b*. The second discharge passage 1000*b* may be connected to the internal air-blowing passage 1890. The second discharge passage 1000*b* may be disposed on a downstream side of the internal air-blowing passage 1890. A portion of the air (Fd2), having passed through the internal air-blowing passage 1890, may flow upward through the second discharge passage 1000*b*. The air (Fd2), having passed through the second discharge passage 1000*b*, may be supplied to an indoor space through the second discharge port 12*b*. A remaining portion of the air (Fs2), having passed through the internal air-blowing passage 1890, may flow to the humidifying assembly 40. The remaining portion of the air (Fs2), having passed through the internal air-blowing passage 1890, may flow to the humidifying chamber 421. The remaining portion of the air (Fd1) introduced into the humidifying chamber 421 may flow through the first discharge passage 1000*a* along with the humidified air generated in the humidifying chamber 421.

The humidified air (Fd1) flowing through the first discharge passage 1000*a* may be supplied to an indoor space through the first discharge port 12*a*.

It is an aspect of the present disclosure to provide a humidifier capable of discharging clean humidified air. It is yet another aspect of the present disclosure to provide a humidifier capable of easily controlling hygiene in the humidifier. It is yet another aspect of the present disclosure to provide a humidifier capable of sterilizing a fan, a filter, and a humidifying chamber. It is yet another aspect of the present disclosure to provide a humidifier capable of preventing ultraviolet light from leaking to the outside. It is further another aspect of the present disclosure to provide a humidifier capable of discharging together humidified air generated in a heating chamber and humidified air generated in a humidifying chamber. The aspects of the present disclosure are not limited to the aforementioned objectives and other objectives not described herein will be clearly understood by those skilled in the art from the following description.

In order to achieve the above aspects, a humidifier according to an embodiment of the present disclosure may sterilize at least one of a filter, a fan, and a humidifier water tank with ultraviolet light. In order to achieve the above aspects, a humidifier according to an embodiment of the present disclosure controls emitting of ultraviolet light based on whether a case is coupled and whether a filter is seated, thereby increasing safety.

In order to achieve the above aspects, a humidifier according to an embodiment of the present disclosure includes: a case; a base disposed below the case; a base cover which is disposed above the base, and to which the case is removably coupled; a humidifying assembly disposed in the case and configured to generate mist; a filter disposed below the humidifying assembly; and a sterilization module disposed on the base cover and configured to emit ultraviolet light, wherein in response to the case being coupled to the base cover and the filter being seated, the sterilization module is configured to emit ultraviolet light to an inner hollow of the filter, thereby preventing a safety accident, and controlling hygiene in the humidifier. The humidifier according to an embodiment of the present disclosure may further include a fan disposed above the filter and causing air, introduced from a circumferential surface of the filter, to flow upward from the filter.

The case may further include: a first case removably coupled to the base cover, and a second case opposite to the first case with respect to the base cover and removably coupled to the base cover, wherein in response to at least one of the first case and the second case being removed from the base cover, the sterilization module may be configured to stop emitting the ultraviolet light. The base cover may include a first button operating in response to the first case being coupled to the base cover, and a second button operating in response to the second case being coupled to the base cover.

The first case may include a first rib protruding from an inner surface of the first case and making contact with the first button; and the second case may include a second rib protruding from an inner surface of the second case and making contact with the second button. The base cover may include a filter cover making contact with a lower surface of the filter, and a cover body coupled to a lower part of the filter cover.

The sterilization module may be disposed between the filter cover and the cover body. The filter cover may include a hole which is recessed downward from an upper surface thereof, and through which the ultraviolet light passes.

The base cover may further include an elastic member connected to the filter cover and the cover body. The filter cover may include a third rib protruding downwards; and the cover body may include a third button that makes contact with the third rib as the elastic member is compressed when the filter is seated on the filter cover, wherein in response to the third button being separated from the third rib, the sterilization module may be configured to stop emitting the ultraviolet light. The sterilization module may be coupled to the filter cover.

The humidifying assembly may include: a humidifying chamber defining a space in which water is contained; a sterilizer configured to emit light to an inside of the humidifying chamber; and reflection plates arranged along a circumferential wall of the humidifying chamber. The reflection plates may be spaced apart from the sterilizer and disposed to face the sterilizer.

The humidifying chamber may include: an inlet through which air is introduced into the humidifying chamber; an outer wall coupled to the inlet; an inner wall spaced apart from the outer wall; and a first side wall connecting the outer wall and the inner wall, wherein the sterilizer may be disposed on the first side wall.

The reflection plates may include an outer reflection plate disposed on the outer wall, and an inner reflection plate disposed on the inner wall. The reflection plates may include dimples recessed in a direction away from an internal space of the humidifying chamber.

According to at least one of the embodiments of the present disclosure, clean humidified air may be discharged. According to at least one of the embodiments of the present disclosure, hygiene in a humidifier may be easily controlled by sterilizing a fan, a filter, and a humidifying chamber. According to at least one of the embodiments of the present disclosure, safety may be enhanced by preventing ultraviolet light from leaking to the outside. According to at least one of the embodiments of the present disclosure, humidified air generated in a heating chamber and humidified air generated in a humidifying chamber are discharged together, thereby providing pleasant, humidified air. The aspects of the present disclosure are not limited to the aforesaid, and other effects not described herein will be clearly understood by those skilled in the art from the following description of the appended claims.

While the preferred embodiments have been particularly shown and described, the present specification shall not be limited to the particular embodiments described above, and it will be understood by an ordinary skilled person in the art that various changes in form and details may be made therein without departing from the spirit and scope of the present invention as defined by the following claims, and the alternative embodiments should not be individually understood from the inventive concept and prospect of the present disclosure.

It will be understood that when an element or layer is referred to as being "on" another element or layer, the element or layer can be directly on another element or layer or intervening elements or layers. In contrast, when an element is referred to as being "directly on" another element or layer, there are no intervening elements or layers present. As used herein, the term "and/or" includes any and all combinations of one or more of the associated listed items.

It will be understood that, although the terms first, second, third, etc., may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section could be termed a second element, component, region, layer or section without departing from the teachings of the present invention.

Spatially relative terms, such as “lower”, “upper” and the like, may be used herein for ease of description to describe the relationship of one element or feature to another element(s) or feature(s) as illustrated in the figures. It will be understood that the spatially relative terms are intended to encompass different orientations of the device in use or operation, in addition to the orientation depicted in the figures. For example, if the device in the figures is turned over, elements described as “lower” relative to other elements or features would then be oriented “upper” relative to the other elements or features. Thus, the exemplary term “lower” can encompass both an orientation of above and below. The device may be otherwise oriented (rotated 90 degrees or at other orientations) and the spatially relative descriptors used herein interpreted accordingly.

The terminology used herein is for the purpose of describing particular embodiments only and is not intended to be limiting of the invention. As used herein, the singular forms “a”, “an” and “the” are intended to include the plural forms as well, unless the context clearly indicates otherwise. It will be further understood that the terms “comprises” and/or “comprising,” when used in this specification, specify the presence of stated features, integers, steps, operations, elements, and/or components, but do not preclude the presence or addition of one or more other features, integers, steps, operations, elements, components, and/or groups thereof.

Embodiments are described herein with reference to cross-section illustrations that are schematic illustrations of idealized embodiments (and intermediate structures). As such, variations from the shapes of the illustrations as a result, for example, of manufacturing techniques and/or tolerances, are to be expected. Thus, embodiments should not be construed as limited to the particular shapes of regions illustrated herein but are to include deviations in shapes that result, for example, from manufacturing.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Any reference in this specification to “one embodiment,” “an embodiment,” “example embodiment,” etc., means that a particular feature, structure, or characteristic described in connection with the embodiment is included in at least one embodiment. The appearances of such phrases in various places in the specification are not necessarily all referring to the same embodiment. Further, when a particular feature, structure, or characteristic is described in connection with any embodiment, it is submitted that it is within the purview of one skilled in the art to effect such feature, structure, or characteristic in connection with other ones of the embodiments.

Although embodiments have been described with reference to a number of illustrative embodiments thereof, it should be understood that numerous other modifications and embodiments can be devised by those skilled in the art that will fall within the spirit and scope of the principles of this disclosure. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. A humidifier, comprising:
a case;
a base disposed below the case;
a base cover which is disposed above the base and to which the case is removably coupled;
a humidifying assembly disposed in the case and configured to generate mist;
a filter disposed below the humidifying assembly; and
a light source disposed on the base cover and configured to emit ultraviolet light toward an inner hollow of the filter when the case is coupled to the base cover and the filter is seated.

2. The humidifier of claim 1, further comprising a fan disposed above the filter and causing air to flow from outside of case to flow through the filter and upward from the filter and toward the humidifying assembly.

3. The humidifier of claim 1,
wherein the case comprises:
a first case removably coupled to the base cover; and
a second case opposite to the first case with respect to the base cover and removably coupled to the base cover, and
wherein in response to at least one of the first case or the second case being uncoupled from the base cover, the light source is configured to stop emitting the ultraviolet light.

4. The humidifier of claim 3, wherein the base cover comprises a first button operating in response to the first case being coupled to the base cover, and a second button operating in response to the second case being coupled to the base cover.

5. The humidifier of claim 4, wherein:
the first case comprises a first rib protruding from an inner surface of the first case and making contact with the first button when the first case is coupled to the base cover; and
the second case comprises a second rib protruding from an inner surface of the second case and making contact with the second button when the second case is coupled to the base cover.

6. The humidifier of claim 1, wherein the base cover comprises a filter cover making contact with a lower surface of the filter, and a cover body coupled to a lower region of the filter cover.

7. The humidifier of claim 6, wherein the light source is disposed between the filter cover and the cover body.

8. The humidifier of claim 6, wherein the filter cover comprises a hole which is recessed downward from an upper surface thereof, and through which the ultraviolet light passes.

9. The humidifier of claim 6, wherein the base cover further comprises an elastic member connected to the filter cover and the cover body.

10. The humidifier of claim 9,
wherein:
the filter cover comprises a third rib protruding downwards, the elastic member is compressed when the filter is seated on the filter cover, and the cover body comprises a third button that makes contact with the third rib when the elastic member is compressed due to the filter being seated on the filter cover, and wherein in response to the third button being separated from the third rib, the light source is configured to stop emitting the ultraviolet light.

11. The humidifier of claim 1, wherein the light source is coupled to the filter cover.

12. The humidifier of claim 1, wherein the light source is a first light source, and wherein the humidifying assembly comprises:

a humidifying chamber in which water is contained;

a second light source configured to emit ultraviolet light to an inside of the humidifying chamber; and reflection plates arranged along a circumferential wall of the humidifying chamber.

13. The humidifier of claim 12, wherein the reflection plates are spaced apart from the second light source and disposed to face the second light source.

14. The humidifier of claim 12, wherein the humidifying assembly comprises:

an inlet through which air is introduced into the humidifying chamber;

an outer wall coupled to the inlet;

an inner wall spaced apart from the outer wall; and a first side wall connecting the outer wall and the inner wall, and wherein the second light source is disposed on the first side wall.

15. The humidifier of claim 14, wherein the reflection plates comprise an outer reflection plate disposed on the outer wall, and an inner reflection plate disposed on the inner wall.

16. The humidifier of claim 12, wherein at least one of the reflection plates comprises dimples recessed in a direction away from an internal space of the humidifying chamber to defuse ultraviolet light emitted by the second light source.

17. The humidifier of claim 12, wherein the second light source is configured to not emit ultraviolet light when either the case is not coupled to the base cover or the filter is not seated.

18. The humidifier of claim 1, further comprising:

a suction port through which air is introduced into the case;

a fan disposed in the case;

an air-blowing passage through which a first portion of air blown by the fan flows, the air-blowing passage bypassing the humidifying assembly;

a humidification passage through which a second portion of air blown by the fan flows after passing through the humidifying assembly, the humidification passage being separated from the air-blowing passage; and a discharge port through which air from the air-blowing passage and the humidification passage are output from the case.

* * * * *